(12) United States Patent
Leuthardt et al.

(10) Patent No.: US 12,171,585 B2
(45) Date of Patent: Dec. 24, 2024

(54) SYSTEM AND METHOD FOR TASK-LESS MAPPING OF BRAIN ACTIVITY

(71) Applicant: Washington University, St. Louis, MO (US)

(72) Inventors: Eric Leuthardt, St. Louis, MO (US); Nicholas Szrama, St. Louis, MO (US); Carl Hacker, St. Louis, MO (US); Tim Laumann, St. Louis, MO (US); Maurizio Corbetta, St. Louis, MO (US); Abraham Z. Snyder, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 18/168,074

(22) Filed: Feb. 13, 2023

(65) Prior Publication Data
US 2023/0181119 A1    Jun. 15, 2023

Related U.S. Application Data

(63) Continuation of application No. 16/383,926, filed on Apr. 15, 2019, now Pat. No. 11,589,826, which is a
(Continued)

(51) Int. Cl.
A61B 5/00        (2006.01)
A61B 5/0536    (2021.01)
(Continued)

(52) U.S. Cl.
CPC .......... *A61B 5/7246* (2013.01); *A61B 5/0022* (2013.01); *A61B 5/0042* (2013.01);
(Continued)

(58) Field of Classification Search
CPC ... A61B 5/7246; A61B 5/0022; A61B 5/0042; A61B 5/0536; A61B 5/055; A61B 5/37;
(Continued)

(56) References Cited

U.S. PATENT DOCUMENTS 6,167,298 A * 12/2000 Levin ................... A61B 5/6803
                                                                  600/545
7,215,122 B2    5/2007 Zhao et al.
(Continued)

OTHER PUBLICATIONS

Wang, J. Zuo X et al., Graph-based network analysis of resting-state functional MRI, Front. Syst. Neurosci, 2010, 4:16, doi: 10.3389/fnsys.2010.00016.
(Continued)

*Primary Examiner* — Bo Joseph Peng
(74) *Attorney, Agent, or Firm* — Armstrong Teasdale LLP

(57) ABSTRACT

A computing device for use in a system for mapping brain activity of a subject includes a processor. The processor is programmed to select a plurality of measurements of brain activity that is representative of at least one parameter of a brain of the subject during a resting state. Moreover, the processor is programmed to compare at least one data point from each of the measurements with a corresponding data point from a previously acquired data set from at least one other subject. The processor is also programmed to produce at least one map for each of the measurements based on the comparison of the resting state data point and the corresponding previously acquired data point. The processor may also be programmed to categorize the brain activity in a plurality of networks in the brain based on the map.

24 Claims, 17 Drawing Sheets
(13 of 17 Drawing Sheet(s) Filed in Color)

Related U.S. Application Data continuation of application No. 16/136,996, filed on Sep. 20, 2018, now Pat. No. 10,258,289, which is a continuation of application No. 15/237,202, filed on Aug. 15, 2016, now Pat. No. 10,092,246, which is a continuation of application No. 13/673,816, filed on Nov. 9, 2012, now Pat. No. 9,480,402.

(60) Provisional application No. 61/558,751, filed on Nov. 11, 2011.

(51) Int. Cl.
| | |
|---|---|
| *A61B 5/055* | (2006.01) |
| *A61B 5/37* | (2021.01) |
| *G01R 33/48* | (2006.01) |
| *G01R 33/56* | (2006.01) |
| *G16H 50/20* | (2018.01) |

(52) U.S. Cl.
CPC ............ *A61B 5/0536* (2013.01); *A61B 5/055* (2013.01); *A61B 5/37* (2021.01); *A61B 5/4064* (2013.01); *A61B 5/742* (2013.01); *G01R 33/4806* (2013.01); *G01R 33/5608* (2013.01); *G16H 50/20* (2018.01); *A61B 2576/026* (2013.01)

(58) Field of Classification Search
CPC . A61B 5/4064; A61B 5/742; A61B 2576/026; G01R 33/4806; G01R 33/5608; G16H 50/20
See application file for complete search history.

(56) References Cited

U.S. PATENT DOCUMENTS

| | | | |
|---|---|---|---|
| 7,469,159 B2 | 12/2008 | Deyoe et al. | |
| 7,715,901 B2 | 5/2010 | Salomon et al. | |
| 7,729,755 B2 | 6/2010 | Laken | |
| 7,894,903 B2 | 2/2011 | John | |
| 8,167,298 B2 | 5/2012 | Ueda | |
| 2003/0229107 A1 | 12/2003 | Cowan et al. | |
| 2004/0096089 A1 | 5/2004 | Borsook et al. | |
| 2006/0074336 A1* | 4/2006 | Grieve ................... | A61B 5/372 600/544 |
| 2006/0173510 A1* | 8/2006 | Besio ...................... | A61B 5/375 607/45 |
| 2007/0010732 A1 | 1/2007 | Deyoe et al. | |
| 2009/0012386 A1 | 1/2009 | Buckner | |
| 2009/0253982 A1 | 10/2009 | Wang | |
| 2009/0292210 A1* | 11/2009 | Culver ................... | G06T 7/0012 600/476 |
| 2011/0301431 A1* | 12/2011 | Greicius ................ | G06T 7/0012 600/300 |

OTHER PUBLICATIONS

Laurienti, P. et al., Modularity maps reveal communite structure in resting human brain, Nat. Prec., 2009, https://doi.org/10.1038/npre.2009.3069.1.

Sankar, T. et al., Functional MRI in Image Guided Neurosurgery, In: Lozano A.M., Gildenberg P.L., Tasker R.R. (eds) Textbook of Stereotactic and Funcational Neurosurgery, Spoinger, Berlin, Heidelberg, 2009, https://doi.org/10.1007/978-3-540-69960-6_20.

Arvid, Lundervoid, On conscieousness, resting state fMRI, and neurodynamics, Nonlinear Biomedical Physics, vol. 4, Article No. S9, Jun. 3, 2010.

Tripoliti et al., A six stage approach for the diagnosis of the Alzheimer's disease based on fMRI data, Journal of Biomedical Informatics 43, 2010, 307-320, Available online Oct. 31, 2009.

Uddin et al., Functional Connectivity of Default Mode Network Components: Correlation, Anticorrelation, and Casuality, Human Brain Mapping, 30:625-637, 2009.

Hovey et al., A Guide to Magnetic Stimulation, The Magstim Company Ltd., Jul. 21, 2006.

Jiang et al., Medical Image analysis with artificial neural networks, Computerized Medical Imaging and Graphics, vol. 34, Issue 8, Dec. 2010, pp. 617-631, Available online Aug. 2010.

Dormont et al., Neuroimaging and Deep Brain Stimulation, Americal Journal of Neuroradiology, Jan. 2010, 31(1) pp. 15-23.

Meunier et al., "Modular and hierarchically modular organization of brain networks," Frontiers in Neuroscience, 4 (Article 200): 1-11 (2010).

Miller et al., "Direct electrophysiological measurement of human default network areas," Procceding of the National Academy of Sciences USA, 106(29): 12174-12177 (2009).

Mueller et al., "An Introduction to Kernel-Based Learning Algorithms," IEEE Transaction on Neural Networks, 12(2): 181-201 (2001).

Murphy et al., "The impact of global signal regression on resting state correlations: are anti-correlated networks introduced?" NeuroImage, 44(3): 893-905 (2009).

Petacchi et al., "Cerebellum and auditory function: an ALE meta-analysis of functional neuroimaging studies," Human Brain Mapping, 25 (1): 118-128 (2005).

Petersen et al., "Positron emission tomographic studies of the cortical anatomy of single-word processing," Nature, 331(6157): 585-589 (1988).

Plaut et al., "Experiments on Learning by Back Propagation," Technical Report CMU-CS-86-126, 1986 (45 pages).

Power et al., "Spurious but systematic correlations in functional connectivity MRI networks arise from subject motion," NeuroImage, 59(3): 2142-2154 (2012).

Power et al., "Functional network organization of the human brain," Neuron, 72(4): 665-678 (2011).

Pravata et al., "Functional connectivity MR imaging of the language network in patients with drug-resistant epilepsy," American Journal of Neuroradiology, 32(3): 532-540 (2010).

Rosenblatt, "The perceptron: a probabilistic model for information storage and organization in the brain," Psychological Review, 65(6): 386-408 (1958).

Rumelhart et al., "Learning representations by back-propagating errors," Nature, 323(9): 533-536 (1986).

Sestieri et al., "Episodic memory retrieval, parietal cortex, and the default mode network: functional and topographic analyses," The Journal of Neuroscience, 31(12): 4407-4420 (2011).

Sestieri et al., "Attention to memory and the environment: functional specialization and dynamic competition in human posterior parietal cortex," The Journal of Neuroscience, 30(25): 8445-8456 (2010).

Sharman et al., "Mapping connectivity in the cortical-subcortical motor circuits of Parkinson's disease patients," UMR-S975, CRICM-INSERM-UPMC-CNRS (1 page).

Shulman et al., "Right hemisphere dominance during spatial selective attention and target detection occurs outside the dorsal frontoparietal network," The Journal of Neuroscience, 30(10): 3640-3651 (2010).

Shulman et al., "Interaction of stimulus-driven reorienting and expectation in ventral and dorsal frontoparietal and basal ganglia-cortical networks," The Journal of Neuroscience, 29(14): 4392-4407 (2009).

Simon "Near-decomposability and complexity: How a mind resides in a brain," in The Mind, the Brain, and Complex Adaptive Systems, H.J. Morowitz (Ed), Santa Fe Institute Studies in the Sciences of Complexity, Proceedings vol. XXII, Reading, MA, pp. 25-43 (1995).

Smith et al., "Correspondence of the brain's functional architecture during activation and rest," Proceedings of the National Academy of Sciences USA, 106(31): 13040-13045 (2009) with Supporting Information, Smith et al. 10.1073/pnas. 0905267106, p. 1-10.

Smyser et al., "Longitudinal Analysis of Neural Network Development in Preterm Infants," Cerebral Cortex, 20(12): 2852-2862 (2010).

Spoormaker et al., "Development of a large-scale functional brain network during human non-rapid eye movement sleep," The Journal of Neuroscience, 30(34): 11379-11387 (2010).

(56) References Cited

OTHER PUBLICATIONS

Spreng, "The fallacy of a "task-negative" network," Frontiers in Psychology, 3(145): 1-5 (2012).
Sylvester et al., "Anticipatory suppression of nonattended locations in visual cortex marks target location and predicts perception," The Journal of Neuroscience, 28(26): 6549-6556 (2008).
Sylvester et al., "Asymmetry of anticipatory activity in visual cortex predicts the locus of attention and perception," The Journal of Neuroscience, 27(52): 14424-14433 (2007).
Sylvester et al., "Anticipatory and stimulus-evoked blood oxygenation level-dependent modulations related to spatial attention reflect a common additive signal," The Journal of Neuroscience, 29(34): 10671-10682 (2009).
Tomasi et al., "Language network: segregation, laterality and connectivity," Molecular Psychiatry, 17(8): 759 (2012).
Tosoni et al., "Distinct representations for shifts of spatial attention and changes of reward contingencies in the human brain," Cortex, 49(6): 1733-1749 (2013).
Van Essen et al., "An integrated software suite for surface-based analyses of cerebral cortex," Journal of the American Medical Informatics Association, 8(5): 443- 459 (2001).
Van Essen et al. "A Population-Average, Landmark-and Surface-based (PALS) Atlas of Human Cerebral Cortex," NeuroImage, 28(3): 635-662 (2005).
Van Dijk et al., "Intrinsic functional connectivity as a tool for human connectomics: theory, properties, and optimization," Journal of Neurophysiology, 103(1): 297-321 (2010).
Walther et al., "Simple line drawings suffice for functional MRI decoding of natural scene categories," Proceedings of the National Academy of Sciences USA, 108(23): 9661-9666 (2011).
Xu et al., "The influence of carbon dioxide on brain activity and metabolism in conscious humans," Journal of Cerebral Blood Flow & Metabolism, 31(1): 58-67 (2011).
Yeo et al., "The organization of the human cerebral cortex estimated by intrinsic functional connectivity," Journal of Neurophysiology, 106(3): 1125-1165 (2011).
Zhang et al., "Intrinsic functional relations between cerebral cortex and thalamus," Journal of Neurophysiology, 100 (4): 1740-1748 (2008).
Fair et al., "A method for using blocked and event-related fMRI data to study "resting state" functional connectivity," NeuroImage, 35(1): 396-405 (2007).
Goldman et al., "Simultaneous EEG and fMRI of the alpha rhythm," Neuroreport., 13(18): 2487-2492 (2002).
Astafiev et al., "Extrastriate body area in human occipital cortex responds to the performance of motor actions", Nature Neuroscience, 7(5): 542-548 (2004).
Barrett et al., "Objective assessment of image quality. III. ROC metrics, ideal observers, and likelihood-generating functions," Journal of the Optical Society of America A: Optics, Image Science, and Vision, 15(6): 1520-1535 (1998).
Beckman et al., "Investigations into resting-state connectivity using independent component analysis," Philosophical transactions of the Royal Society of London Series B, 360(1457): 1001-1013 (2005).
Binder et al., "Mapping anterior temporal lobe language areas with FMRI: a multicenter normative study," NeuroImage, 54(2): 1465-1475 (2011).
Biswal et al., "Functional connectivity in the motor cortex of resting human brain using echo-planer MRI," Magnetic Resonance Medicine, 34(4): 537-541 (1995).
Boly et al.; "Hierarchical clustering of brain activity during human nonrapid eye movement sleep," Proceedings of the National Academy of Sciences USA, 109(15): 5856-5861 (2012).
Briganti et al., "Reorganization of Functional Connectivity of Language Network in Patients with Brain Gliomas," American Journal of Neuroradiology, 33(10): 1983-1990 (2012).
Buckner, "The serendipitous discovery of the brain's default network," NeuroImage, 62(2): 1137-1145 (2012).

Buckner et al., "The organization of the human cerebellum estimated by intrinsic functional connectivity," Journal of Neurophysiology, 106(5): 2322-2345 (2011).
Corbetta et al., "Voluntary orienting is dissociated from target detection in human posterior parietal cortex," Nature Neuroscience, 3(3): 292-297 (2000).
Dale et al., "Cortical surface-based analysis. I. Segmentation and surface reconstruction," NeuroImage, 9(2): 179-194 (1999).
Damoiseaux et al., "Reduced resting-state brain activity in the "default network" in normal aging," Cerebral Cortex, 18(8): 1856-1864 (2008).
Damoiseaux et al., "Consistent resting-state networks across healthy subjects," Proceedings of the National Academy of Sciences USA, 103(37): 13848-13853 (2006).
Damoiseaux et al., "Greater than the sum of its parts; a review of studies combining structural connectivity and resting-state functional connectivity," Brain Structure & Function, 213(6): 525-533 (2009).
Dosenbach et al.. "Distinct brain networks for adaptive and stable task control in humans," Proceedings of the National Academy of Sciences USA, 104(26): 11073-11078 (2007).
Dosenbach et al., "A Core System for the Implementation of Task Sets," Neuron, 50(50): 799-812 (2006).
Dosenbach et al., "A dual-networks architecture of top-down control," Trends in Cognitive Sciences, 12(3): 99-105 (2008).
Doucet et al., "Brain activity at rest: a multiscale hierarchical functional organization," Journal of Neurophysiology, 105(6): 2753-2763 (2011).
Dunmar et al., "Learning and Generalization in a Linear Perceptron Stochastically Trained with Noisy Data," Journal of Physics A: Mathematical and General, 26(21): 5767-5779 (1993).
Fair et al., "Functional brain networks develop from a "local to distributed" organization," PLoS Computational Biology, 5(5): 1-14 (2009).
Fox et al., "The human brain is intrinsically organized into dynamic, anticorrelated functional networksm," Proceedings of the National Academy of Sciences USA, 102(27): 9673-9678 (2005).
Fox et al., "The global signal and observed anticorrelated resting state brain networks," Journal of Neurophysiology, 101(6): 3270-3283 (2009).
Fox et al., "Spontaneous neuronal activity distinguishes human dorsal and ventral attention systems," Proceedings of the National Academy of Sciences USA, 103(26): 10046-10051 (2006).
Fox et al., "Clinical applications of resting state functional connectivity," Frontiers in Systems Neuroscience, 4(Article 19): 1-13 (2010).
Fox et al., "Spontaneous fluctuations in brain activity observed with functional magnetic resonance imaging," Nature Reviews Neuroscience, 8(9): 700-711 (2007).
Ganmor et al., "Sparse low-order interaction network underlies a highly correlated and learnable neural population code," Proceedings of the National Academy of Sciences USA, 108(23): 9679-9684 (2011).
Gaona et al., "Nonuniform High-Gamma (60-500 Hz) Power Changes Dissociate Cognitive Task and Anatomy in Human Cortex," The Journal of Neuroscience, 31(6): 2091-2100 (2011).
Geman et al., "Stochastic relaxation, gibbs distributions, and the bayesian restoration of images," IEEE Transactions on Pattern Analysis and Machine Intelligence, PAMI-6(6): 721-741 (1984).
Guimera et al., "Cartography of complex networks; modules and universal roles," Journal of Statistical Mechanics: Theory and Experiment, 2005(P02001): 1-17 (2005).
Hampson et al., "Connectivity-behavior analysis reveals that functional connectivity between left BA39 and Broca's area varies with reading ability," NeuroImage, 31(2): 513-519 (2006).
He et al., "Breakdown of functional connectivity in frontoparietal networks underlies behavioral deficits in spatial neglect," Neuron, 53(6): 905-918 (2007).
He et al., "Electrophysiological correlates of the brain's intrinsic large-scale functional architecture," Proceedings of the National Academy of Sciences USA, 105(41): 16038-16044 (2008).

(56) References Cited

OTHER PUBLICATIONS

Hickok et al., "Dorsal and ventral streams: a framework for understanding aspects of the functional anatomy of language," Cognition, 92: 67-99 (2004).

Hill et al., "Similar patterns of cortical expansion during human development and evolution," Proceedings of the National Academy of Sciences USA, 107(29): 13135-13140 (2010).

Hornik et al., "Multilayer Feedforward Networks Are Universal Approximators," Neural Networks, 2(5): 359-366 (1989).

Kahn et al., "Distinct cortical anatomy linked to subregions of the medial temporal lobe revealed by intrinsic functional connectivity," Journal of Neurophysiology, 100(1): 129-139 (2008).

Kincade et al., "An event-related functional magnetic resonance imaging study of voluntary and stimulus-driven orienting of attention," The Journal of Neuroscience, 25(18): 4593-4604 (2005).

Kirkpatrick, "Optimization by Simulated Annealing: Quantitative Studies," Journal of Statistical Physics, 34(5): 975-986 (1984).

Kirkpatrick et al., "Optimization by Simulated Annealing," Science, 220(4598): 671-680 (1983).

Kupinski et al., "Experimental determination of object statistics from noisy images," Journal of the Optical Society of America A: Optics, Image Science, and Vision, 20(3): 421-429 (2003).

Le Cun et al., "Handwritten Digit Recognition: Applications of Neural Network Chips and Automatic Learning," IEEE Communications Magazine, 27(11): 41-46 (1989).

Le Cun et al., "Backpropagation Applied to Handwritten Zip Code Recognition," Neural Computation, 1(4): 541-551 (1989).

Lee et al., "Clustering of resting state networks," PLoS One, 7(7): 1-12 (2012).

Lemm et al., "Introduction to machine learning for brain imaging," NeuroImage, 56(2): 387-399 (2011).

Lippmann, "Pattern-Classification Using Neural Networks," IEEE Communications Magazine, 27(11): 47-64 (1989).

Lippmann, "Review of Neural Networks for Speech Recognition," Neural Computation, 1(1): 1-38 (1989).

Logothetis et al. "Interpreting the BOLD signal," Annual Review of Physiology, 66: 735-769 (2004).

Marrelec et al., "Regions, systems, and the brain: Hierarchical measures of functional integration in fMRI," Medical Image Analysis, 12(4): 484-496 (2008).

Marrelec et al., "Assessing the influence of different ROI selection strategies on functional connectivity analyses of 'fMRI data acquired during steady-state conditions," PLoS One, 6(4): 1-14 (2011).

Mennes et al., "Inter-individual differences in resting-state functional connectivity predict task-induced BOLD activity," NeuroImage, 50(4): 1690-1701 (2010).

* cited by examiner

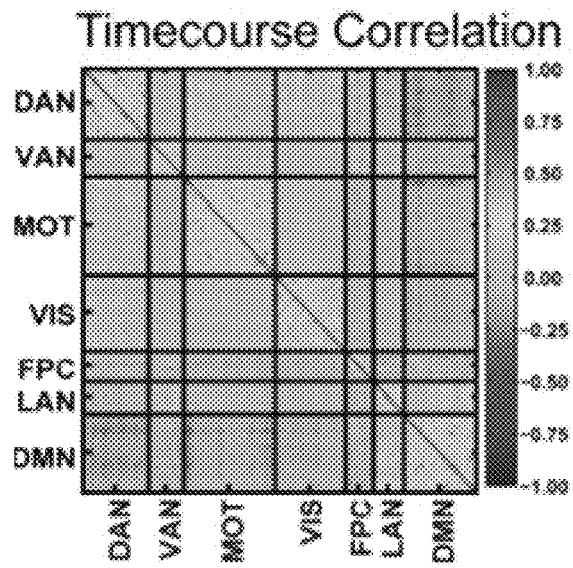
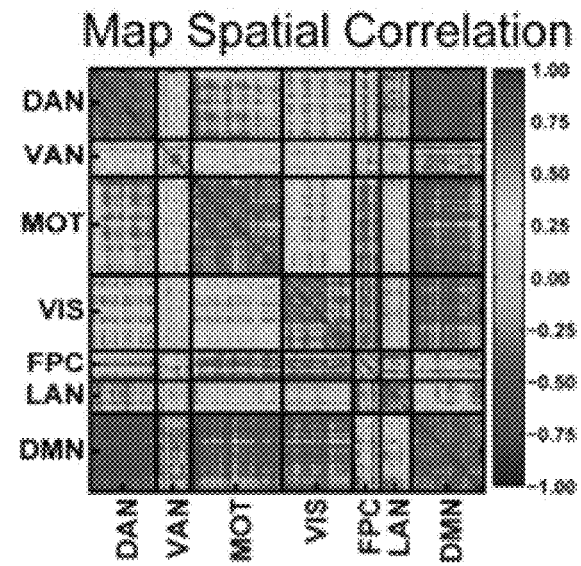
FIG. 8A  FIG. 8B
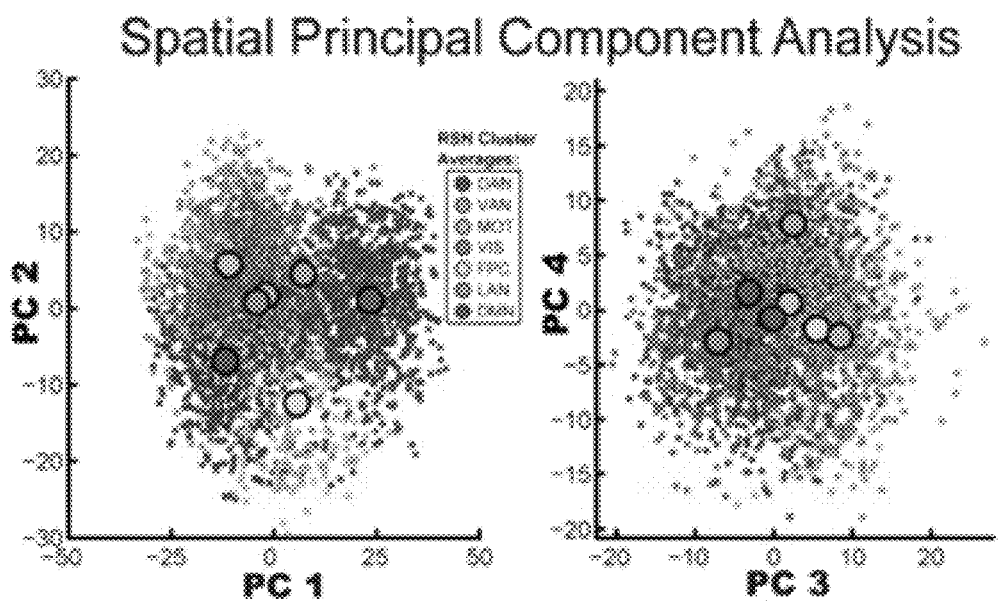
FIG. 8C  FIG. 8D

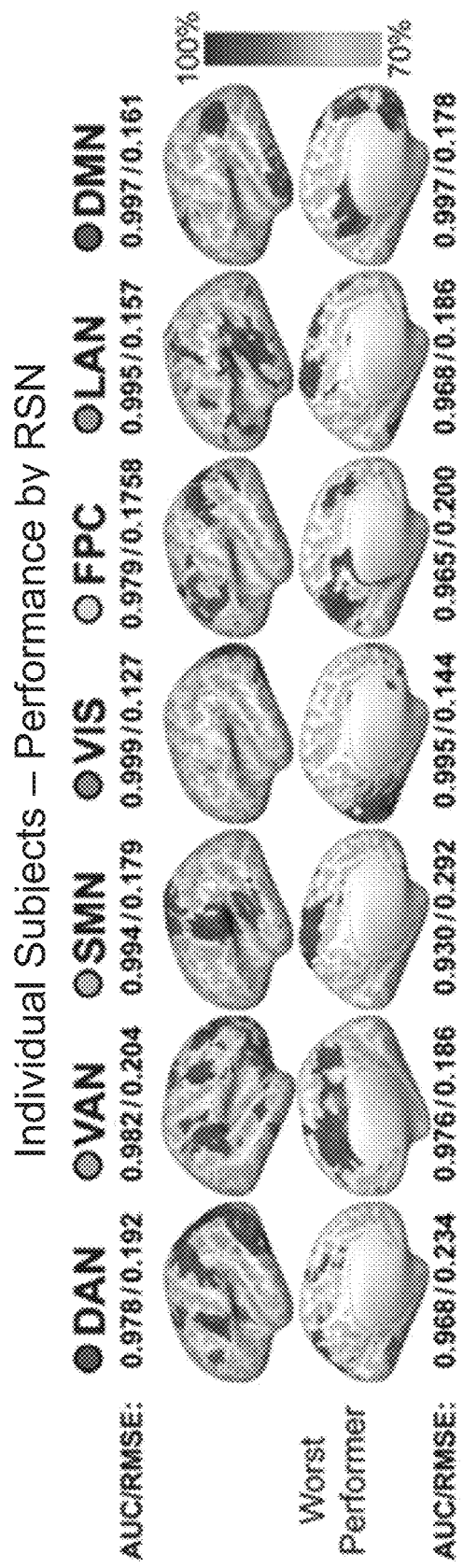
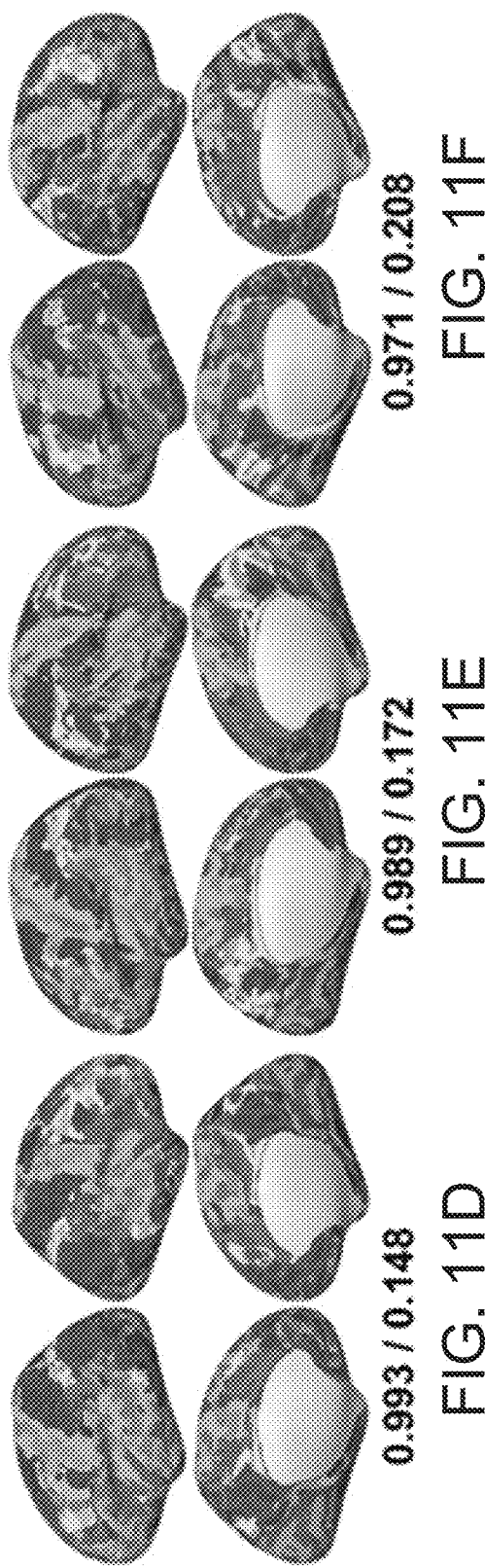
FIG. 11C
FIG. 11D
FIG. 11E
FIG. 11F

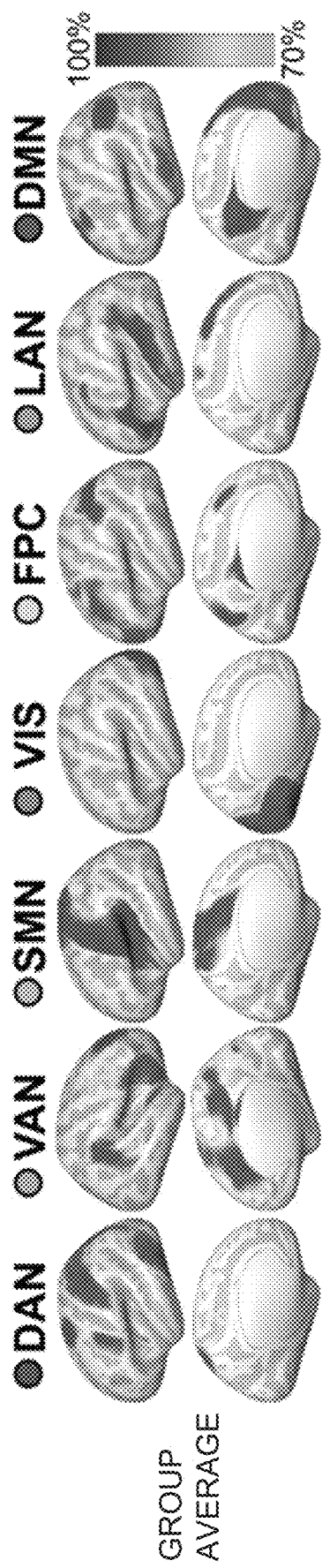
FIG. 12A GROUP AVERAGE
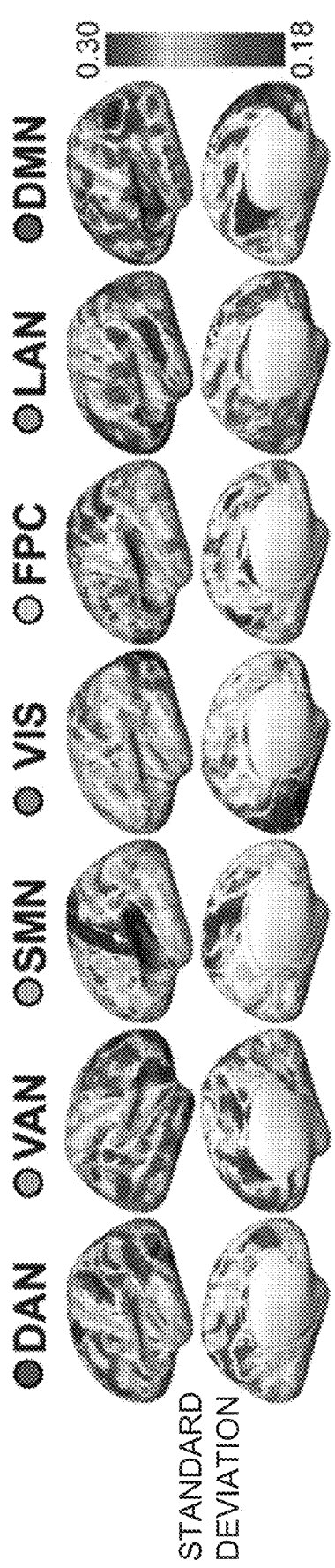
FIG. 12B STANDARD DEVIATION
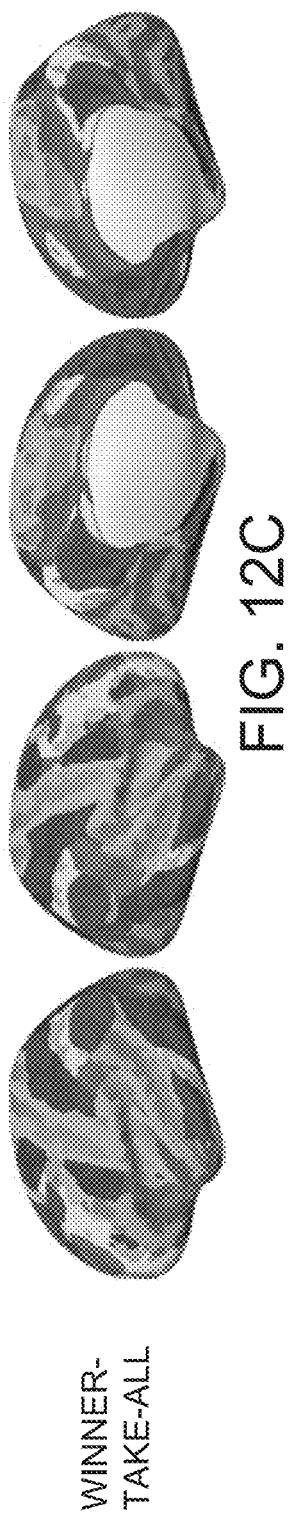
FIG. 12C WINNER-TAKE-ALL

SYSTEM AND METHOD FOR TASK-LESS MAPPING OF BRAIN ACTIVITY

CROSS REFERENCE TO RELATED APPLICATION

This application is a continuation of U.S. application Ser. No. 16/383,926 filed Apr. 15, 2019 and incorporated herein by reference in its entirety, U.S. application Ser. No. 16/383,926 is a continuation of U.S. application Ser. No. 16/136,996, filed Sep. 20, 2018, patented as U.S. Pat. No. 10,258,289 and incorporated herein by reference in its entirety. U.S. application Ser. No. 16/136,996 is a continuation of U.S. application Ser. No. 15/237,202, filed Aug. 15, 2016, patented as U.S. Pat. No. 10,092,246 and incorporated herein by reference in its entirety. U.S. application Ser. No. 15/237,202 is a continuation of U.S. application Ser. No. 13/673,816, filed Nov. 9, 2012, patented as U.S. Pat. No. 9,480,402 and incorporated herein by reference in its entirety. U.S. application Ser. No. 13/673,816 claims priority to U.S. Provisional Application Ser. No. 61/558,751, filed Nov. 11, 2011, and also incorporated herein by reference in its entirety.

BACKGROUND

The field of the invention relates generally to brain mapping systems and, more particularly, to systems and methods for task-less mapping of brain activity using resting state data collected from a brain of a subject.

Brain mapping includes a set of neuroscience techniques that are predicated on the mapping of biological quantities or properties onto spatial representations of a subject's brain resulting in at least one map. At least some known neuroimaging systems or techniques are used frequently in clinical and research settings for brain mapping such that brain function can be monitored. For example, functional magnetic resonance imaging (fMRI) may be used to enable researchers and clinicians to see visual images of the brain, wherein the images may be used to identify brain activity within a plurality of networks of the brain. One approach includes a task based technique wherein the fMRI may be used to detect correlations between brain activation and various tasks that a subject performs during a scan. Such task-based techniques can be useful in clinical applications. For example, the images obtained through fMRI may enable a surgeon to identify portions of the brain that are responsible for various functions and the surgeon may attempt to avoid contact with such portions while performing surgery on the brain.

However, task-based neuroimaging may not be suitable for all segments of a clinical population. For example, a toddler or a nervous patient may be unable to comprehend and/or perform various tasks. It was recently discovered, via fMRI, that even during the absence of overt tasks, fluctuations in brain activity are correlated across functionally-related cortical regions. Thus, the spatial and temporal evaluations of spontaneous neuronal activity has allowed mapping of these resting-state networks (RSNs) with a task-less technique. For this technique, at least one voxel within the image obtained by the fMRI is selected and a correlation analysis is performed to identify other voxels that correspond with the selected voxel. However, it may be challenging to identify which voxel to select. For example, an individual would require a great deal of expertise and resources to select a relevant voxel. In fact, selecting a voxel and/or processing information to select a voxel can be time consuming.

Accordingly, it is desirable to provide a system and method that can readily identify the voxels to select and, at substantially the same time, provide suitable results for accurate brain mapping.

BRIEF DESCRIPTION

In one aspect, a computing device for use in a system for mapping brain activity of a subject generally comprises a processor. The processor is programmed to select a plurality of measurements of brain activity that is representative of at least one parameter of a brain of the subject during a resting state. Moreover, the processor is programmed to compare at least one data point from each of the measurements with a corresponding data point from a previously acquired data set from at least one other subject. The processor is also programmed to produce at least one map for each of the measurements based on the comparison of the resting state data point and the corresponding previously acquired data point. The processor may also be programmed to categorize the brain activity in a plurality of networks in the brain based on the map.

In another aspect, a system for mapping brain activity of a subject generally comprises a sensing system and a computing device that is coupled to the sensing system. The sensing system is configured to detect a plurality of measurements of brain activity that is representative of at least one parameter of a brain of the subject during a resting state. The computing device includes a communication interface that is configured to receive at least one signal representative of the measurements, and a processor that is coupled to the communication interface. The processor is programmed to select the measurements of brain activity. Moreover, the processor is programmed to compare at least one data point from each of the measurements with a corresponding data point from a previously acquired data set from at least one other subject. The processor is also programmed to produce at least one map for each of the measurements based on the comparison of the resting state data point and the corresponding previously acquired data point. The processor may also be programmed to categorize the brain activity in a plurality of networks in the brain based on the map.

In yet another aspect, a method for mapping brain activity of a patient generally comprises selecting, via a processor, a plurality of measurements of brain activity that is representative of at least one parameter of a brain of the subject during a resting state. At least one data point from each of the plurality of measurements is compared, via the processor, with a corresponding data point from a previously acquired data set from at least one other subject. At least one map is produced, via the processor, for each of the measurements based on the comparison of the resting state data point and the corresponding previously acquired data point. The brain activity is categorized, via the processor, in a plurality of networks in the brain based on the map.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 8A-8D are graphs depicting correlation maps;

FIGS. 11A-11F are schematics of topographies in individual subjects;

FIGS. 12A-12C are schematics of classification results;

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE DRAWINGS

The exemplary systems, apparatus, and methods described herein overcome at least some known disadvantages associated with at least some known brain mapping techniques, such as task-based and/or task-less systems. More specifically, the embodiments described herein include a computing device for use in a system for mapping brain activity of a subject that generally comprises a processor. The processor is programmed to select a plurality of measurements of brain activity that is representative of at least one parameter of a brain of the subject during a resting state. Moreover, the processor is programmed to compare at least one data point from each of the measurements with a corresponding data point from a previously acquired data set from at least one other subject. The processor is also programmed to produce at least one map for each of the measurements based on the comparison of the resting state data point and the corresponding previously acquired data point. The processor may also be programmed to categorize the brain activity in a plurality of networks in the brain based on the map. By using previously acquired data points to categorize the brain activity in a plurality of networks in the brain of the subject, task-based techniques can be avoided. Moreover, by having the processor select the plurality of measurements, a user may no longer need to spend a considerable amount of time determining which measurements, such as voxels, to select.

Figure 1:
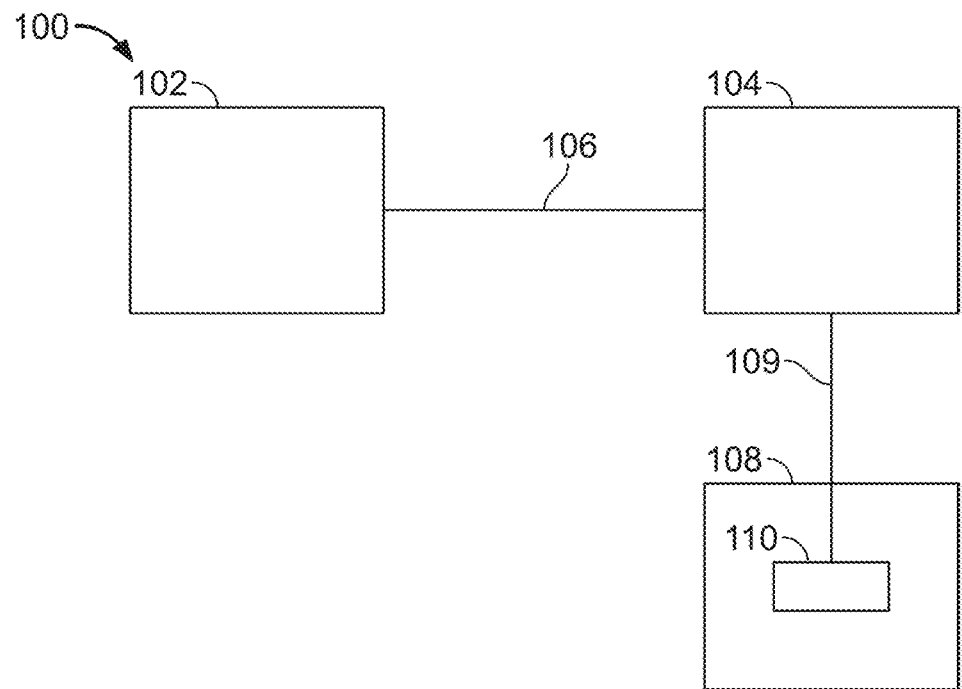
FIG. 1 is a block diagram of an exemplary system for task-less mapping of brain activity.

FIG. 1 illustrates an exemplary system 100 for mapping brain activity of a subject (not shown). It should be noted that the term "brain activity" as used herein includes the various activities within a brain of the subject that correspond to various tasks performed by the subject. For example, the brain transmits and receives signals in the form of hormones, nerve impulses, and chemical messengers that enable the subject to move, eat, sleep, and think. In the exemplary embodiment, system 100 is used to identify locations within a plurality of networks within the brain that are responsible for such brain activities.

As seen in FIG. 1, system 100 includes a sensing system 102 that is configured to detect a plurality of measurements of brain activity that is representative of at least one parameter of the brain of the subject during a resting state. In one suitable embodiment, sensing system 102 is a magnetic resonance imaging device (MRI) that is configured to generate at least one spectroscopic signal representative of a plurality of measurements of brain activity that is representative of at least one parameter of the brain of the subject during a resting state. More specifically, sensing system 102 may generate an altered magnetic field within the brain to measure various parameters of the brain. In another suitable embodiment, sensing system 102 may be a specialized MRI, such as a functional magnetic resonance imaging (fMRI) device that is used to measure a variation in blood flow (hemodynamic response) related to neural activity in the brain or spinal cord (not shown) of the subject. In yet another suitable embodiment, sensing system 102 may be an electrocorticography device having at least one electrode (not shown) to measure at least one voltage fluctuation within the brain. It should be noted that the present disclosure is not limited to any one particular type of imaging and electrical technique or device, and one of ordinary skill in the art will appreciate that the current disclosure may be used in connection with any type of technique or device that enables system 100 to function as described herein.

In the exemplary embodiment, system 100 also includes a computing device 104 coupled to sensing system 102 via a data conduit 106. It should be noted that, as used herein, the term "couple" is not limited to a direct mechanical, electrical, and/or communication connection between components, but may also include an indirect mechanical, electrical, and/or communication connection between multiple components. Sensing system 102 may communicate with computing device 104 using a wired network connection (e.g., Ethernet or an optical fiber), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, N.Y. WIMAX is a registered trademark of WiMax Forum, of Beaverton, Oreg. BLUETOOTH is a registered trademark of Bluetooth SIG, Inc. of Kirkland, Wash.

In the exemplary embodiment, computing device 104 is configured to receive at least one signal representative of a plurality of measurements of brain activity from sensing system 102. More specifically, computing device 104 is configured to receive at least one signal representative of an altered magnetic field within the brain of the subject from sensing system 102. Alternatively, computing device 104 may be configured to receive at least one signal representative of at least one voltage fluctuation within the brain from at least one electrode.

System 100 also includes a data management system 108 that is coupled to computing device 104 via a network 109. Data management system 108 may be any device capable of accessing network 109 including, without limitation, a desktop computer, a laptop computer, or other web-based connectable equipment. More specifically, in the exemplary embodiment, data management system 108 includes a database 110 that includes previously acquired data of other subjects. In the exemplary embodiment, database 110 can be fully or partially implemented in a cloud computing environment such that data from the database is received from one or more computers (not shown) within system 100 or remote from system 100. In the exemplary embodiment, the previously acquired data of the other subjects may include, for example, a plurality of measurements of brain activity that is representative of at least one parameter of a brain of each of the subjects during a resting state. Database 110 can also include any additional information of each of the subjects that enables system 100 to function as described herein.

Data management system 108 may communicate with computing device 104 using a wired network connection (e.g., Ethernet or an optical fiber), a wireless communication means, such as, but not limited to radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a cellular phone technology (e.g., the Global Standard for Mobile communication (GSM)), a satellite communication link, and/or any other suitable communication means. More specifically, in the exemplary embodiment, data management system 108 transmits the data for the subjects to computing device 104. While the data is shown as being stored in database 110 within data management system 108, it should be noted that the data of the subjects may be stored in another system and/or device. For example, computing device 104 may store the data therein.

During operation, while the subject is in a resting state, sensing system 102 uses a magnetic field to align the magnetization of some atoms in the brain of the subject and radio frequency fields to systematically alter the alignment of this magnetization. As such, rotating magnetic fields are produced and are detectable by a scanner (not shown) within sensing system 102. More specifically, in the exemplary embodiment, sensing system 102 detects a plurality of measurements of brain activity that is representative of at least one parameter of the brain of the subject during the resting state. Sensing system 102 also generates at least one spectroscopic signal representative of the plurality of measurements and transmits the signal(s) to computing device 104 via data conduit 106. Moreover, data of other subjects may be transmitted to computing device 104 from database 110 via network 109. As explained in more detail below, computing device 104 produces at least one map, such as a functional connectivity map, for each of the measurements based on a comparison of at least one resting state data point of the subject and a corresponding data point from the previously acquired data set from at least one other subject. Computing device 104 uses the map to categorize or classify the brain activity in a plurality of networks in the brain.

Figure 2:
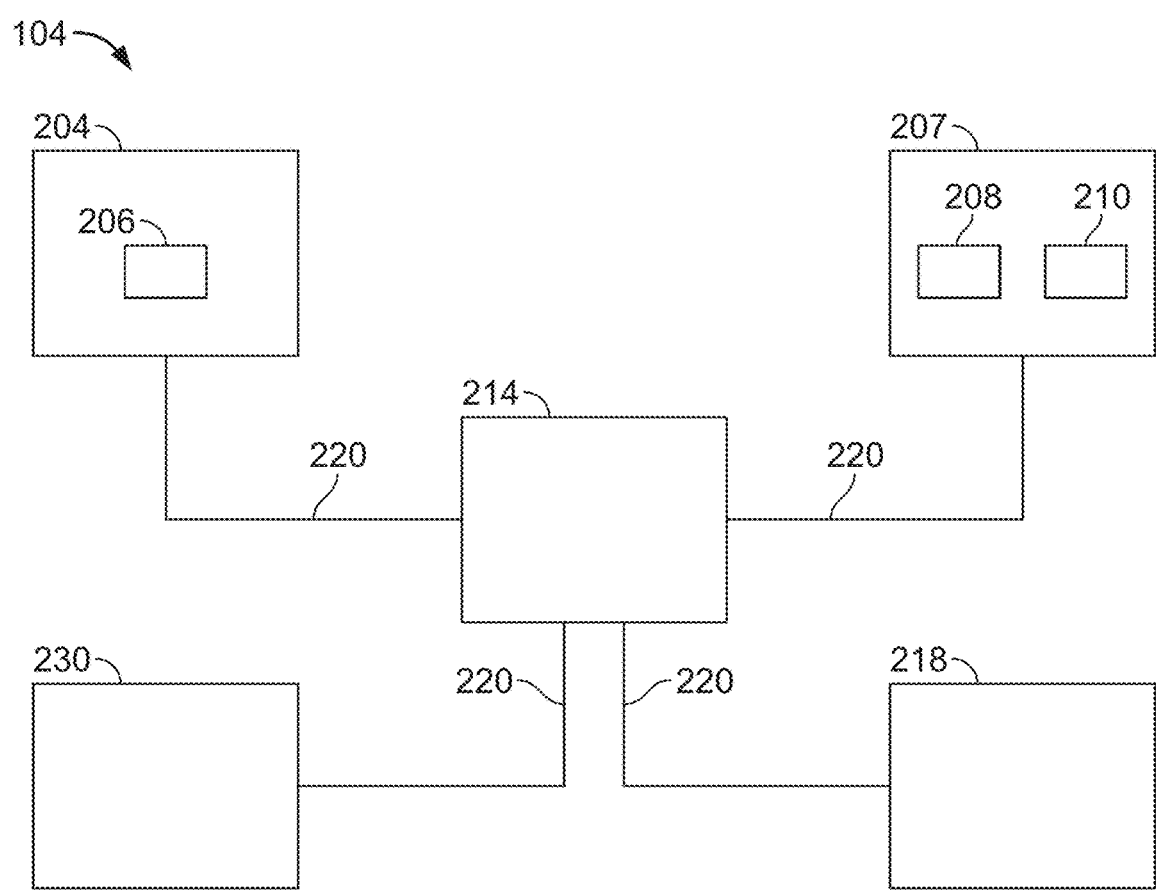
FIG. 2 is a block diagram of an exemplary computing device of the system shown in FIG. 1.

FIG. 2 is a block diagram of computing device 104. In the exemplary embodiment, computing device 104 includes a user interface 204 that receives at least one input from a user, such as an operator of sensing system 102 (shown in FIG. 1). User interface 204 may include a keyboard 206 that enables the user to input pertinent information. User interface 204 may also include, for example, a pointing device, a mouse, a stylus, a touch sensitive panel (e.g., a touch pad, a touch screen), a gyroscope, an accelerometer, a position detector, and/or an audio input interface (e.g., including a microphone).

Moreover, in the exemplary embodiment, computing device 104 includes a presentation interface 207 that presents information, such as input events and/or validation results, to the user. Presentation interface 207 may also include a display adapter 208 that is coupled to at least one display device 210. More specifically, in the exemplary embodiment, display device 210 may be a visual display device, such as a cathode ray tube (CRT), a liquid crystal display (LCD), an organic LED (OLED) display, and/or an "electronic ink" display. Alternatively, presentation interface 207 may include an audio output device (e.g., an audio adapter and/or a speaker) and/or a printer.

Computing device 104 also includes a processor 214 and a memory device 218. Processor 214 is coupled to user interface 204, presentation interface 207, and to memory device 218 via a system bus 220. In the exemplary embodiment, processor 214 communicates with the user, such as by prompting the user via presentation interface 207 and/or by receiving user inputs via user interface 204. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 218 includes one or more devices that enable information, such as executable instructions and/or other data, to be stored and retrieved. Moreover, memory device 218 includes one or more computer readable media, such as, without limitation, dynamic random access memory (DRAM), static random access memory (SRAM), a solid state disk, and/or a hard disk. In the exemplary embodiment, memory device 218 stores, without limitation, application source code, application object code, configuration data, additional input events, application states, assertion statements, validation results, and/or any other type of data. Computing device 104, in the exemplary embodiment, may also include a communication interface 230 that is coupled to processor 214 via system bus 220. Moreover, communication interface 230 is communicatively coupled to sensing system 102 and to data management system 108 (shown in FIG. 1).

In the exemplary embodiment, processor 214 may be programmed by encoding an operation using one or more executable instructions and providing the executable instructions in memory device 218. In the exemplary embodiment, processor 214 is programmed to select a plurality of measurements that are received from sensing system 102 of brain activity that is representative of at least one parameter of the brain of the subject during a resting state. The plurality of measurements may include, for example, a plurality of voxels of at least one image of the subject's brain, wherein the image may be generated by processor 214 within computing device 104. The image may also be generated by an imaging device (not shown) that may be coupled to computing device 104 and sensing system 102, wherein the imaging device may generate the image based on the data received from sensing system 102 and then the imaging device may transmit the image to computing device 104 for storage within memory device 218. Alternatively, the plurality of measurements may include any other type measurement of brain activity that enables system 100 to function as described herein.

Processor 214 may also be programmed to perform a correlation analysis. More specifically, in the exemplary embodiment, processor 214 may be programmed to compare at least one data point from each of the plurality of measurements with a corresponding data point from a previously acquired data set from at least one other subject. For example, processor 214 may be programmed to compare a resting state data point from each selected voxel from an image of the subject with a corresponding data point that is located within the same voxel of the previously acquired data set of the other subject. Processor 214 may also be programmed to produce at least one map (not shown in FIG. 2) of the brain of the subject, such as a functional connectivity map, for each of the plurality measurements. The map is based on the comparison of the resting state data point and the corresponding previously acquired data point. The map, for example, may illustrate the location within the brain of a measured brain activity. Processor 214 may be programmed to produce the map by using the various compared data points in a known algorithm to calculate a plurality of outputs, such as, for example, at least one output vector. One algorithm that may be used is represented in Equation 1 below.

$$\text{input}_1 = \tanh^{-1}\left(\left[\frac{\ln(1/\text{output}^{-1})}{-a}\right] \cdot \frac{pinv(\text{Weights}_{hidden-output})}{a}\right) \cdot \frac{pinv(\text{Weights}_{input-hidden})}{b} \quad \text{(Eq. 1)}$$

In Equation 1, a and b represent activating function parameters. The output represents a seven dimensional output vector and pinv represents a pseudo inverse function.

Processor 214 may also be programmed to categorize or classify the measured brain activity in a plurality of networks in the brain based on the map. For example, processor 214 may be programmed to categorize the measured brain activity to a particular neural network of the brain of the subject based on the location of the measured brain activity on the map of the subject's brain.

During operation, as the subject is in a resting state, sensing system 102 detects a plurality of measurements of brain activity that is representative of at least one parameter of the brain of the subject. Sensing system 102 transmits at least one signal representative of the measurements to computing device 104 via data conduit 106. More specifically, the signals are transmitted to and received by communication interface 230 within computing device 104. Communication interface 230 then transmits the signals to processor 214 for processing and/or to memory device 218, wherein the data may be stored and transmitted to processor 214 at a later time. Processor 214 may generate an image of the plurality of measurements. Alternatively, sensing system 102 may transmit the signals to an imaging device (not shown), wherein an image of the measurements may be generated. The image may then be transmitted to computing device 104, wherein the image is stored within memory device 218 and transmitted to processor 214 for processing.

Moreover, data of other subjects may be transmitted to computing device 104 from database 110 (shown in FIG. 1) via network 109 (shown in FIG. 1). More specifically, the data may be received by communication interface 230 and then transmitted to processor 214 for processing and/or to memory device 218, wherein the data may be stored and transmitted to processor 214 at a later time. Computing device 104 may obtain the data at any time during operation.

In the exemplary embodiment, computing device 104 produces at least one map for each of the plurality of measurements received. More specifically, processor 214 first selects each of the plurality of measurements, received from sensing system 102. For example, in the exemplary embodiment, processor 214 selects each of the voxels from the image. Alternatively, processor 214 may select any other types of measurements for brain activity that enables system 100 to function as described herein. Moreover, a user may see the image on the computing device 104, via presentation interface 207, and select the measurements, such as voxels, via user interface 204.

When each of the measurements has been selected, processor 214 then performs a correlation analysis. More specifically, processor 214 compares at least one data point from each of the selected measurements with a corresponding data point from a previously acquired data set from at least one other subject, wherein computing device 104 obtained the data set from database 110. For example, processor 214 may compare at least one resting state data point from each selected voxel of the image of the subject with a data point that is located within the same voxel of the previously acquired data set of at least one other subject.

When processor 214 has completed the correlation analysis, processor 214 then produces at least one map (not shown in FIG. 2) of the brain of the subject, such as a functional connectivity map, for each of the measurements. More specifically, processor 214 produces a map of the brain of the subject based on each of the comparisons of each of the resting state data points and the corresponding previously acquired data points. The map, for example, may illustrate the location within the brain of a measured brain activity. Processor 214 then categorizes or classifies the measured brain activity in a plurality of networks in the brain based on the map. For example, based on the location of the measured brain activity in the map, processor 214 categorizes the measured brain activity to a particular neural network of the brain of the subject. The map may be presented to the user via presentation interface 207. Moreover, a textual representation and/or a graphical output for the various categorizations may also be presented to the user via presentation interface 207.

Figure 3:
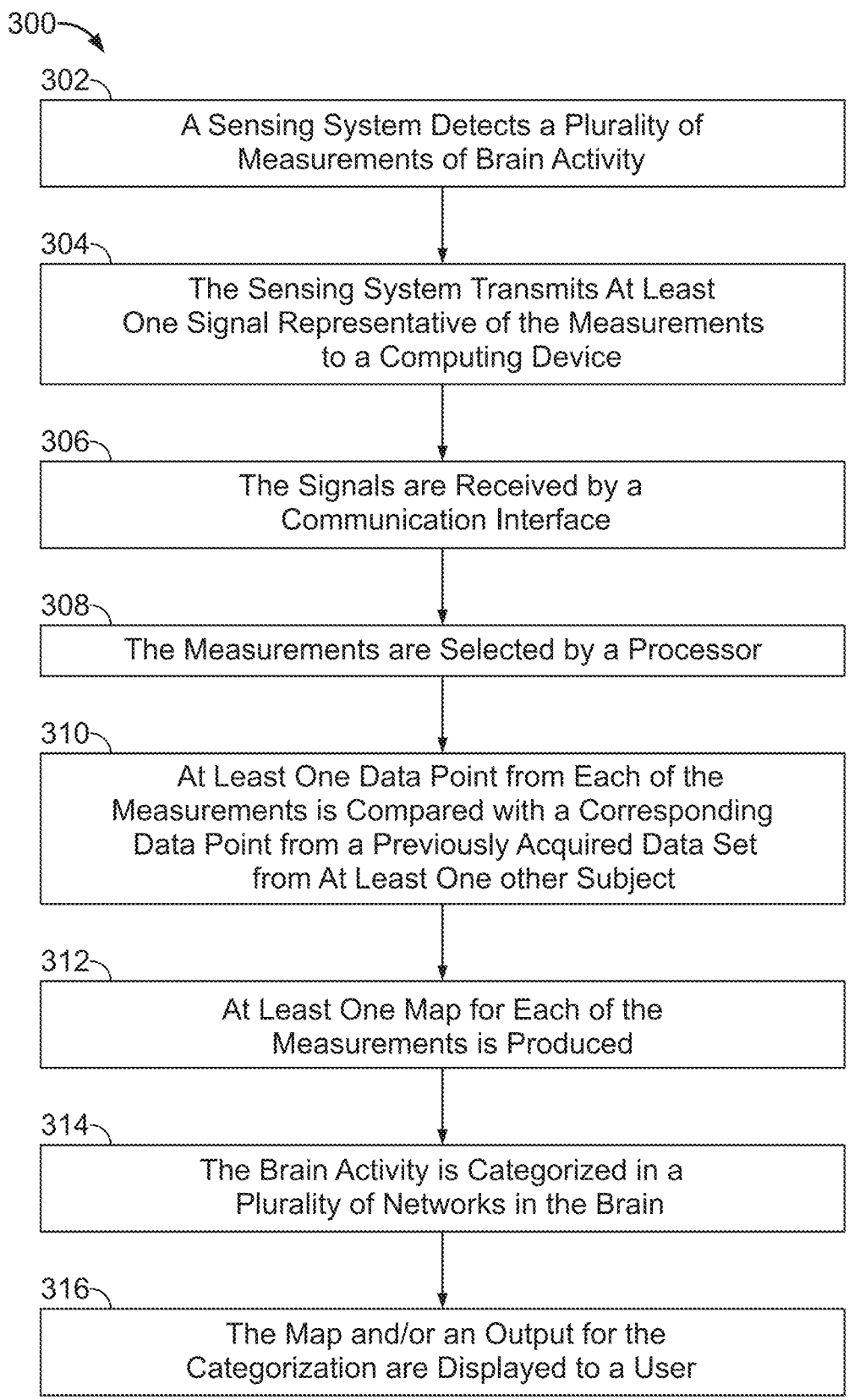
FIG. 3 is flow diagram of an exemplary method for task-less mapping of brain activity using the system shown in FIG. 1.

FIG. 3 is flow diagram of an exemplary method 300 for task-less mapping of brain activity of a brain of a subject using system 100 (shown in FIG. 1). A sensing system 102 (shown in FIG. 1) detects 302 a plurality of measurements of brain activity that is representative of at least one parameter of the brain of the subject during a resting state. Sensing system 102 transmits 304 at least one signal representative of the measurements to a computing device 104 (shown in FIGS. 1 and 2). The signals are received 306 by a communication interface 230 (shown in FIG. 2). The measurements are selected 308 by a processor 214 (shown in FIG. 2). At least one data point from each of the measurements is compared 310 with a corresponding data point from a previously acquired data set from at least one other subject. At least one map for each of the measurements is produced 312 based on the comparison of the resting state data point and the corresponding previously acquired data point. The brain activity is categorized 314 in a plurality of networks in the brain based on the map. The map and/or an output for the categorization are displayed 316 to a user, via a presentation interface 207 (shown in FIG. 2).

The embodiments of the system and method for task-less mapping of brain activity using resting state data of a brain of a subject, as described herein, were used in the following exemplary experiment.

Experiment

In the exemplary experiment, perceptron training and testing used data sets previously acquired at the Neuroimaging Laboratories at the Washington University School of Medicine in St. Louis, Mo. All patients were young adults screened to exclude neurological impairment and psychotropic medications. Demographic information and acquisition parameters are given in Table 1 below.

TABLE 1

Characteristics of the training test and validation data sets.

| Dataset | Training | Optimization (Test) | Validation |
|---|---|---|---|
| Number of Subjects | 21 (7M + 14 F) | 17 (8M + 9F) | 10 (4M + 6F) |
| Age | 27.6 (23-35) years | 23.1 (18-27) years | 23.3 ± 3 years |
| Number of frames | 128 × 6 runs | 194 × 4 runs | 100 × 9 runs |
| TR (s) | 2.16 | 2.16 | 3.03* |

*The TR in the validation data set includes a one second pause between frames to accommodate simultaneous EEG recording.

In the exemplary experiment, all imaging was performed with a 3T Allegra scanner. Functional images were acquired using a BOLD contrast sensitive gradient echo echo-planar sequence [FOV=256 mm, flip angle=90°, 4 mm$^3$ voxels, other parameters listed in Table 1] during which subjects were instructed to fixate on a visual cross-hair, remain still, and not fall asleep. Anatomical imaging included one sagittal T1-weighted magnetization prepared rapid gradient echo (MP-RAGE) scan (T1 W) and one T2-weighted scan (T2 W).

Initial fMRI preprocessing followed conventional practice known in the art. This included compensation for slice-dependent time shifts, elimination of systematic odd-even slice intensity differences due to interleaved acquisition, and rigid body correction for head movement within and across runs. Atlas transformation was achieved by composition of affine transforms connecting the fMRI volumes with the T2 W and T1 W structural images. Head movement correction was included with the atlas transformation in a single resampling that generated volumetric time series in 3 mm$^3$ atlas space. Additional preprocessing in preparation for correlation mapping included spatial smoothing (6 mm FWHM Gaussian blur in each direction), voxel-wise removal of linear trends over each fMRI run, and temporal low-pass filtering retaining frequencies below 0.1 Hz.

Spurious variance was reduced by regression of nuisance waveforms derived from head motion correction and time-series extracted from regions (of "non-interest") in white matter and CSF. Nuisance regressors included also the BOLD timeseries averaged over the brain, i.e., global signal regression (GSR). Thus, all computed correlations were effectively order 1 partial correlations controlling for variance shared across the brain. GSR has been criticized on the grounds that it artificially generates anticorrelations. However, GSR fits well as a step preceding principal component analysis because it generates approximately zero-centered correlation distributions. As well, GSR enhances the spatial specificity in subcortical seed regions and reduces structured noise. The question of whether the left tail of a zero-centered correlation distribution ("anticorrelations") is "false" or "tenuously interpretable" is irrelevant in the context of RSN classification.

Correlation maps were computed using standard seed-based procedures, i.e., by correlating the timeseries averaged over all voxels within the seed (generally, 5 mm spheres) against all other voxels, excluding the first 5 (pre-magnetization steady-state) frames of each fMRI run. Frame-censoring was employed with a threshold of 0.5% RMS frame-to-frame intensity change. Frame-censoring excluded 3.8±1.1% of all magnetization steady-state frames from the correlation mapping computations. Correlation maps were Fisher z-transformed prior to further analyses.

In the exemplary embodiment, Cortical reconstruction and volume segmentation were performed using FreeSurfer. Adequate segmentation was verified by inspection of the FreeSurfer-generated results in each of the 21 training and 17 test datasets. Cortical and subcortical gray matter regions were selected from these segmentations, thresholded to obtain a conjunction of 30% of subjects, and then masked with an image of the average BOLD signal intensity across all subjects, thresholded at 80% of the mode value. This last step removes from consideration brain areas in which the BOLD signal is unreliable because of susceptibility artifacts. The resulting 30,981 voxels constituted the grey matter mask. This mask was applied to all correlation maps input to the classifier. Individual surfaces were deformed to a common space, producing consistent assignment of surface vertex indices with respect to gyral features across subjects. Final volumetric results for each subject were sampled onto surface vertices by cubic spline interpolation onto mid-thickness cortical surface coordinates.

Seed regions were generated by meta-analyses of task-fMRI studies. Task-response foci were initially assigned to one of 10 functional networks in Table 2 below. Each task fMRI study contributed a variable number of foci (Task ROIs column in Table 2). Task foci were used as seeds to generate correlation maps in all 21 subjects in the training set. These maps then were entered into random effects analyses (against the null hypothesis of no correlation) to produce Gaussianized t-statistic (Z-score) images. Z-score images representing seeds assigned to the same RSN were averaged. Additionally, a conjunction image representing at least 70% of random effects images for a given network (after thresholding at |Z|>3) was produced. Averaged Z-score images were masked to include only voxels contained in the conjunction. Peaks of the conjunction-masked average were selected as center coordinates for 6 mm spherical ROIs. Accordingly, the constraint employed was that all ROIs within a given network must be separated by at least 12 mm. This process resulted in a large set of ROIs that were operationally treated as provisional.

TABLE 2

Studies of functional co-activation used to generate seed ROIs.

| RSN | Task paradigm | fMRI contrast | Task ROIs | Provisional seed ROIs | Final seed ROIs |
|---|---|---|---|---|---|
| DAN | 1. Rapid Serial Visual Presentation (RSVP) 2. Rapid Serial Visual Presentation (RSVP) 3. Posner Cueing Task | 1. Cue Type × event time 2. Cue location × cue type × event time 3. Event time | 10 | 28 | 28 |
| VAN | Posner Cueing Task | Invalid vs. Valid | 2 | 19 | 15 |
| CO* | Mixed design (10 different tasks) | Graph theoretic analysis* | N/A | 7 | |
| SMN | Posner Cueing Task | Target Period | 11 | 37 | 39 |
| AN | Various auditory stimuli | Stimulation vs. control | 2 | 12 | |
| VIS | Visual Localizer | Peripheral | 8 | 19 | 30 |
| | | Foveal | 2 | 12 | |
| FPC* | Mixed design (10 different tasks) | Graph theoretic analysis* | N/A | 11 | 12 |
| LAN | Perceptual vs. Episodic Memory Search Paradigm | Sentence Reading | 13 | 17 | 13 |
| DMN | Perceptual vs. Episodic Memory Search Paradigm | Memory Retrieval | 4 | 42 | 32 |

*Regions reported were themselves the result of a meta-analysis followed by refinement. Hence, these seeds were directly used as provisional ROIs.

In the exemplary embodiment, the provisional ROI set was iteratively refined by maximizing the spatial concordance between the correlation map obtained from each seed and the map obtained by pooling all seeds within the RSN to which the seed was assigned. Pooled seed correlation maps were computed by averaging the time series across all seeds assigned to each RSN. The single seed and the pooled seed maps were averaged across subjects. RSN concordance was assessed as the spatial correlation between the (subject-averaged) single seed and the (subject-averaged) pooled seed maps. Seeds were considered outliers if their concordance estimate was less than 1.5 times the inter-quartile range below the median of all other seeds in the RSN. Outlier seeds were reassigned to the RSN of greatest concordance, unless they were maximally concordant with the currently assigned RSN, in which case they were removed entirely. After reassignment and outlier rejection, new individual seed and pooled seed correlation maps were re-computed and the process was iterated. Convergence (no reassignments or outlier rejections) was achieved in 7 iterations. The cingulo-opercular (CO) network did not survive iterative refinement, and most seeds were reassigned to the ventral attention network or removed. Similarly, the auditory network was subsumed into the sensorimotor network and the originally distinct foveal and peripheral visual networks were combined into a single (VIS) network.

Figure 4:
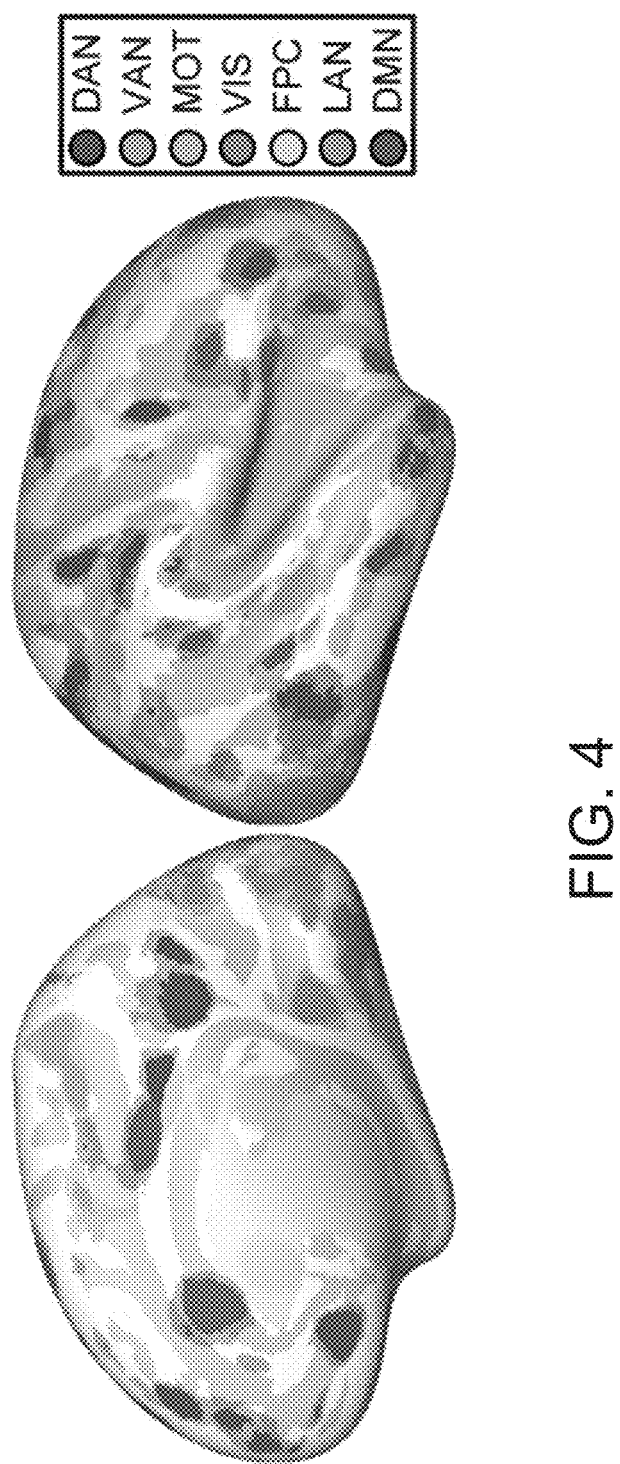
FIG. 4 is an image of seed ROIs for generation of correlation map data.
Figure 15:
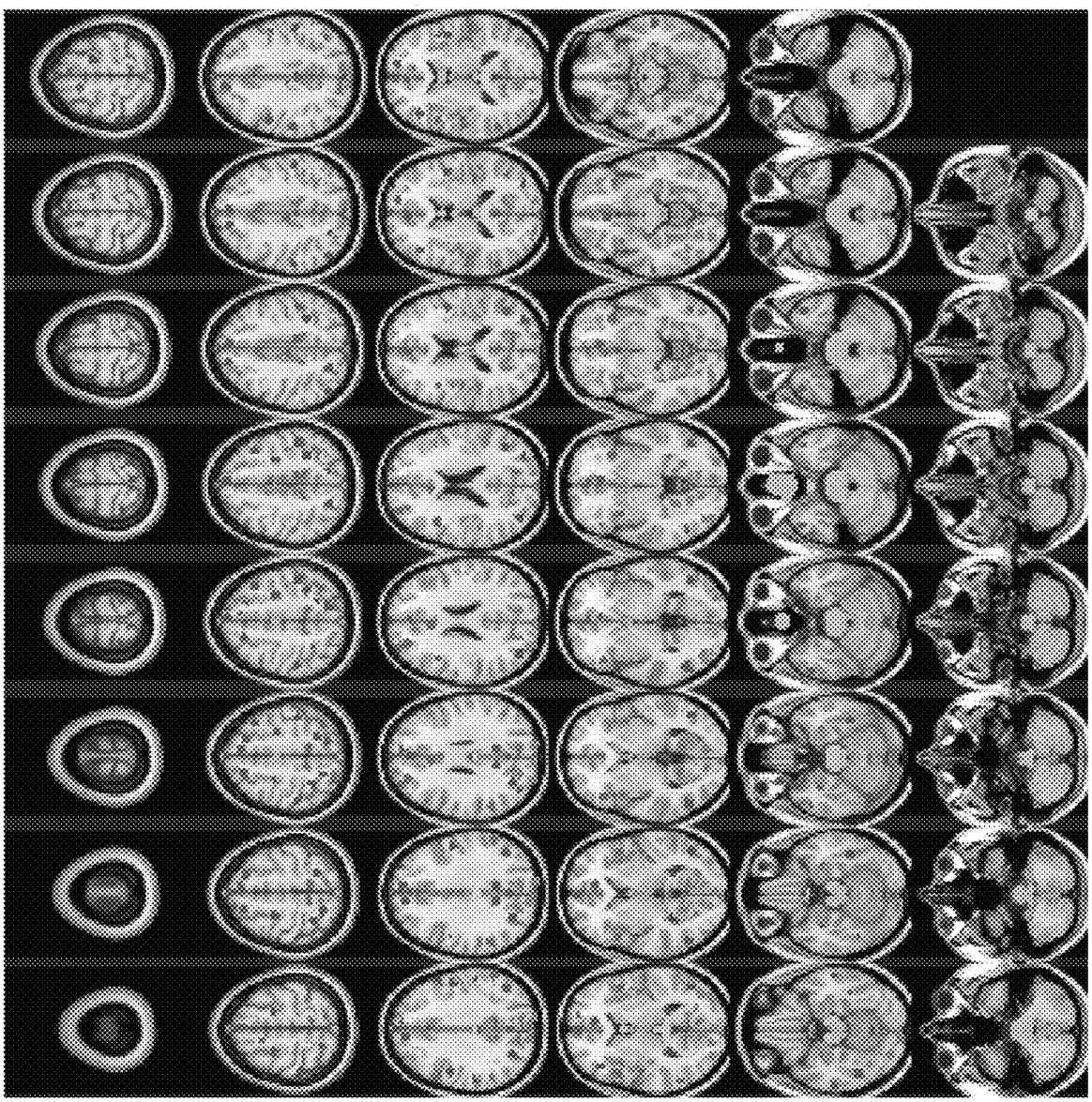
FIG. 15 is a scan of voxels.

Iterative refinement yielded 169 ROIs representing 7 RSNs with high intra- and low inter-network correlation, as shown in FIGS. 4 and 15. To these were added a nuisance category consisting of 6 ROIs in CSF spaces. The latter enabled the classifier to separate correlation patterns representing CSF vs. true RSNs. Computing correlation maps for each of the 175 seed regions in all 21 training subjects produced 3,675 images that were used as training data. Each image in the training set was masked to include only grey matter voxels, producing a 3,675×30,981 matrix. Similarly, 175·17=2,975 images were computed in the test data set. Each image was assigned to one RSN (see the description of iterative seed ROI refinement above and Table 2).

A multilayer perceptron was constructed to classify resting-state fMRI correlation maps into 7 canonical spatial patterns predefined as resting-state networks. The core of the perceptron is an artificial neural network that includes an input, hidden, and output layer, each consisting of some number of nodes fully connecting to the next layer (all-to-all feed-forward). Training samples (correlation maps from a particular seed and subject) are passed into this feed-forward network and the output is compared to the correct RSN label, as specified in the fMRI task meta-analysis. The error in this comparison is used to update the connections, or weights, between layers to increase the performance of the classifier.

As an initial pre-processing step, the dimensionality of the input data was reduced by using principal component analysis (PCA). Representing correlation maps in terms of eigenvectors provides efficient computation, well-conditioned weight matrices, and a free parameter to represent the complexity of the input data (number of PCs). PCA was performed on the matrix of masked correlation images (21 subjects×175 seeds=3,675 images×30,981 voxels for PCA). Each correlation map in the training (3,675 images) and the test (2,975 images) data sets were then represented using a variable number of principal components (PCs).

Figure 5:
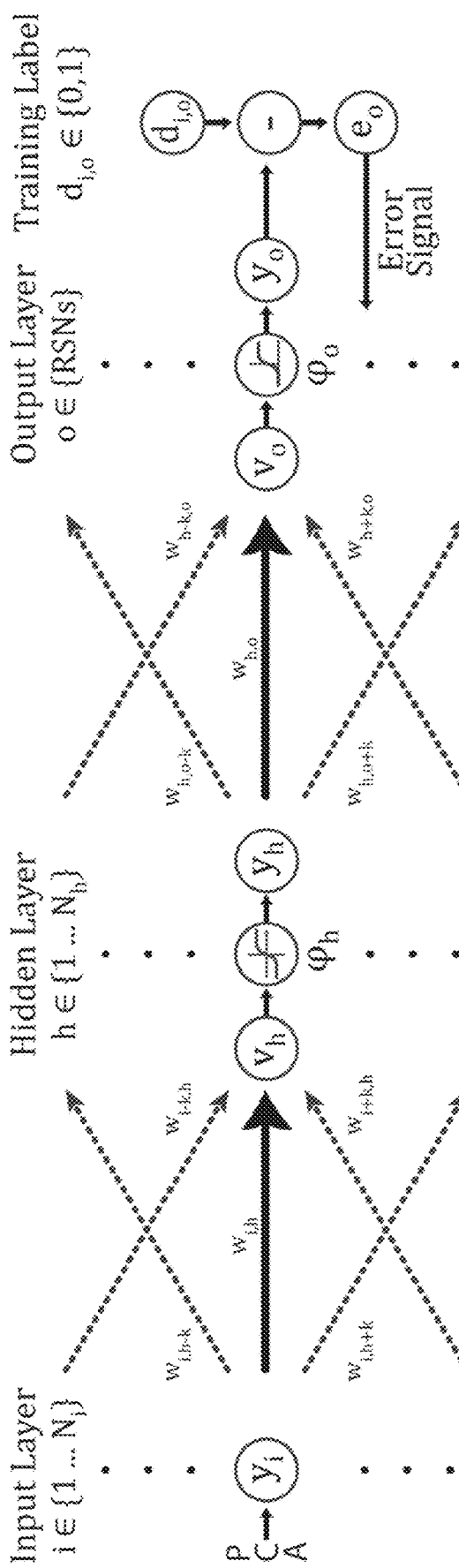
FIG. 5 is a schematic of an exemplary standard multi-layer perceptron architecture and transfer function of the perceptron.

The input layer received the correlation map training data as vectors in PCA space (the value of a given correlation map projected along a particular PC). Thus, the number of input nodes was a free parameter that depended on the number of PCs used to represent the data. Each training example (a correlation map from a particular seed ROI/subject pair) was associated with a desired output value, $d_o$ (Eq. (7)), corresponding to the a priori RSN labels. The goal of the training process is to compare the output to these desired values, thereby generating an error signal used to update connection weights. The overall transfer function of the perceptron (Eq. (2)) corresponds to the detailed schematic of the propagation of inputs through the perceptron (FIG. 5, see legend for symbol definitions).

$$y_o = \varphi_o\left(\sum_h w_{ho}(\eta) \cdot \varphi_h\left(\sum_i w_{ih} \cdot y_i\right)\right) \quad (2)$$

The total input to each hidden node, $v_h$, is determined by the sum of all input nodes, weighted by the feed-forward connections (Eq. (3)). This sum is then transformed by the hidden layer activation function to compute the output value of the hidden layer node, $y_h$ (Eq. (4)).

$$v_h = \sum_i w_{ih} \cdot y_i \qquad (3)$$

$$y_h = \varphi_h(v_h) = a \cdot \tanh(b \cdot v_h) \qquad (4)$$

The output layer nodes operate in the same manner as hidden layer nodes (Eqs. (5) and (6)):

$$v_o(n) = \sum_i w_{ho}(n) \cdot y_h(n) \qquad (5)$$

$$y_o = \varphi_o(v_o) = \frac{1}{1+e^{-a \cdot v_o}} \qquad (6)$$

The After propagation of the input data through the perceptron, the output value for each node, $y_o$, was compared to the desired value, $d_o$, to find the error, $e_o$ (Eq. (7)).

$$e_o(k) = d_o(k) - y_o(k) \qquad (7)$$

The local gradient of the error at an output node is found by the product of this error and the inverse of the activating function applied to the output value:

$$\delta_o = e_o \cdot \varphi_o'(v_o) \qquad (8)$$

where the prime notation indicates the first derivative. After every iteration (n), the weights for the hidden to output layer connections were adjusted in the direction opposite of the gradient of the error:

$$w_{ho}(k+1) = w_{ho}(k) + \eta(k) \cdot \delta_o(k) \cdot y_h(k) \qquad (9)$$

where $\eta$ is the learning rate, $y_h$ is the value of hidden layer node h, and $\delta_o$ is local error gradient at output node o. Similarly, the weights to the hidden layer from the input layer, $w_{ih}$, are adjusted according to Eq. (10).

$$w_{ih}(k+1) = w_{ih}(k) + \eta(k) \cdot \delta_h(k) \cdot y_i(k) \qquad (10)$$

The local gradient at a hidden node, $\delta_h$, may be computed by back-propagation from the output layer.

$$\delta_h = -\frac{dE}{d\gamma_h} = \varphi_h'(v_h) \cdot \sum_o \delta_o \cdot w_{ho} \qquad (11)$$

Figure 6:
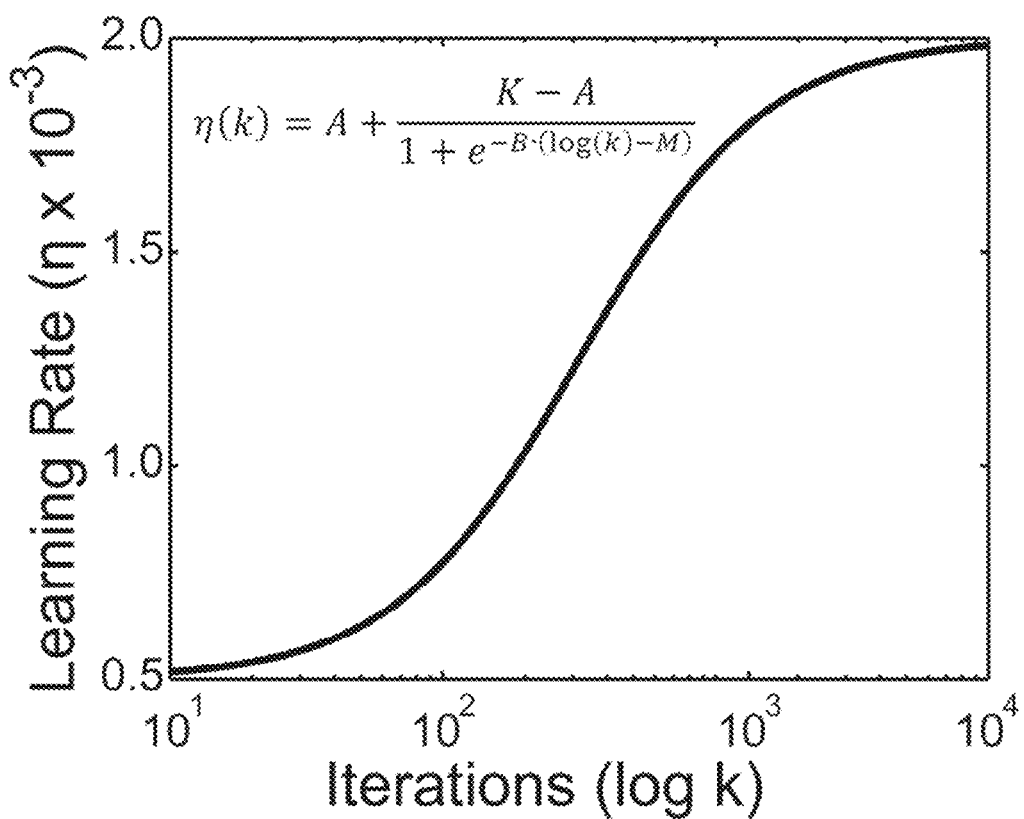
FIG. 6 is a graph of a learning rate.

The learning rate parameter, $\eta$, was set empirically. A range of stable values was determined for a constant $\eta$, where instability was noted as divergence or rapid oscillation of classifier weights. The present results were obtained using an adaptive learning rate that increased as a sigmoid in log iteration index (FIG. 6). The initial learning rate was small ($\eta(0) = A = 5 \cdot 10^{-4}$) to allow the classifier to begin a gentle descent in error gradient towards a stable solution. The learning rate increased exponentially (B=−3, Q =0.5), until saturating at an empirically determined upper limit of stability to ($\eta(\infty) = 2 \cdot 10^{-3}$).

Separation of classes was quantified using receiver operator characteristic analysis. Across a range of thresholds, the proportion of within-class output values above the threshold (true positive fraction, TPF) were compared to the number of out-of-class values above the threshold (false positive fraction, FPF). The TPF as a function of FPF defines the ROC curve. The area under the ROC curve (AUC) was used as a summary statistic of classification performance for each RSN class.

Figure 9A:
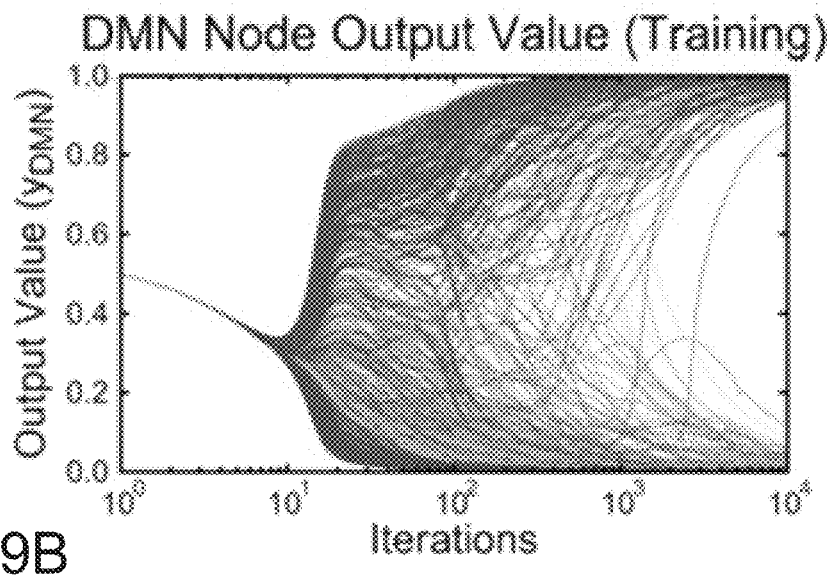
FIGS. 9A-9F are graphs depicting performance levels.
Figure 9B:
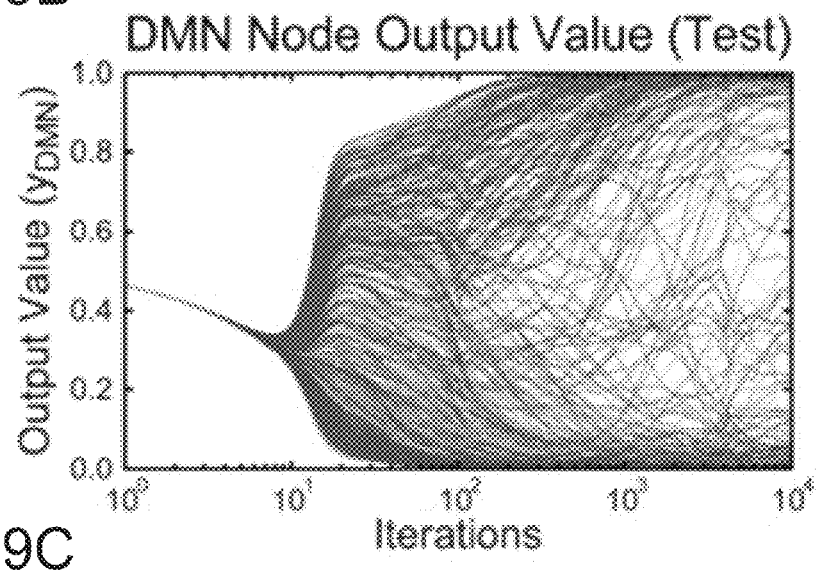
Figure 9C:
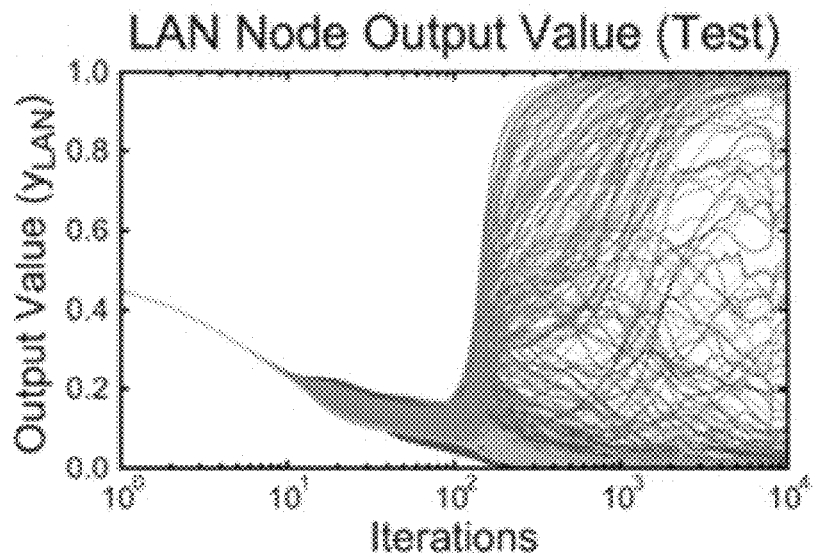
Figure 9D:
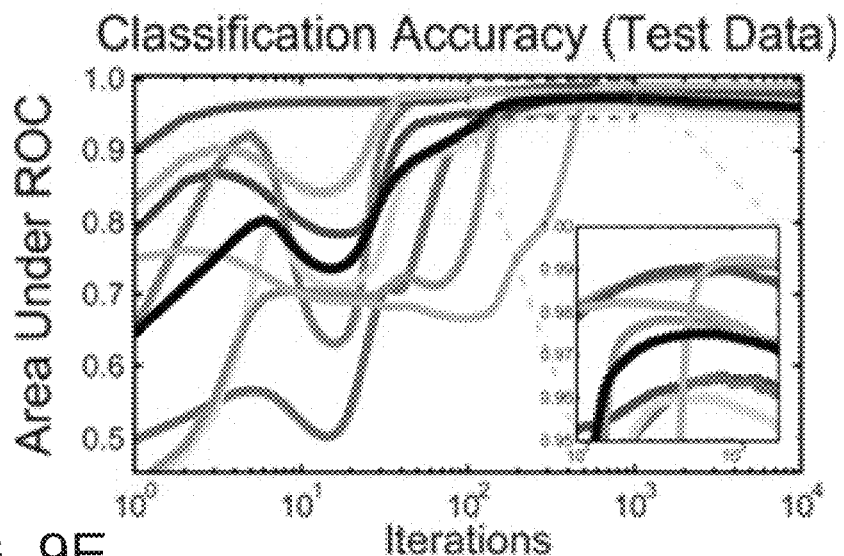

At logarithmically spaced intervals during the training process, training was paused and AUCs were calculated in a separate test data set. This procedure produced training trajectories indicating the relative performance for each RSN (FIG. 9D) throughout the training process. Peak performance for a given RSN was defined at the iteration producing the maximum AUC value in the test data (FIG. 9D). Overall performance was calculated as the average of AUC values across networks (FIG. 9D).

Figure 10:
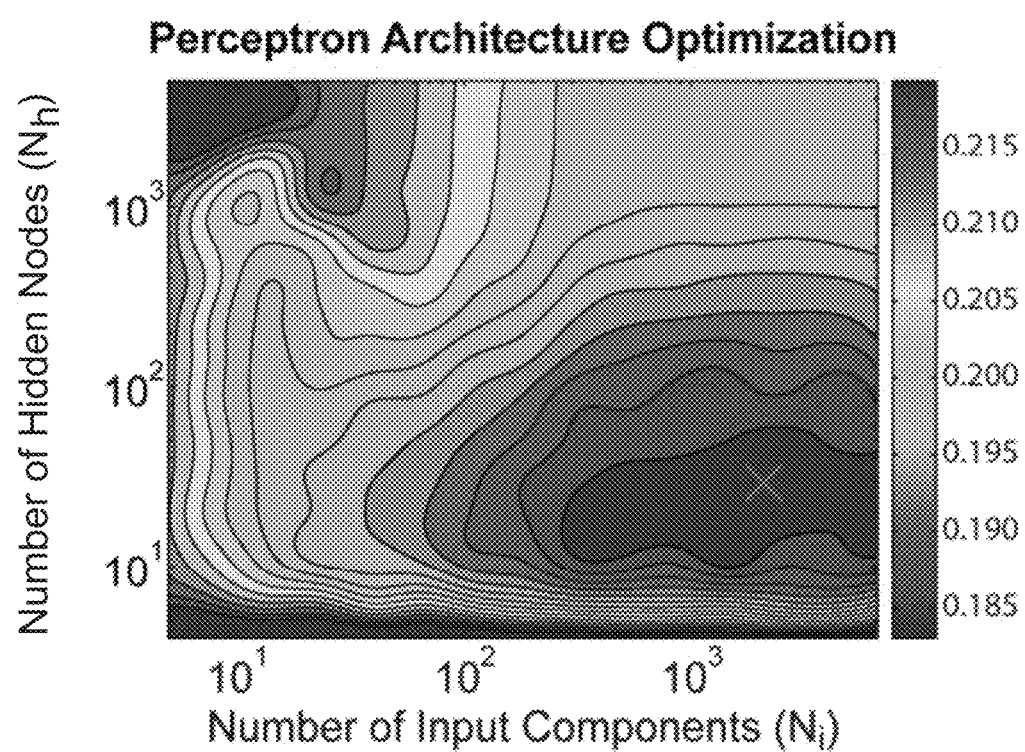
FIG. 10 is a graph depicting search space for perceptron architecture.

In the exemplary embodiment, the number of PCs sampled ($N_i$), and the number of nodes in the hidden layer ($N_h$) constitute hyper-parameters subject to optimization. Overall RMS error was evaluated over a densely sampled $N_i \in [5, 6600] \times N_h \in [4, 5000]$ space. For each ($N_i$, $N_h$) coordinate, a classifier was trained until test set error reached a minimum. The architecture with the least error (minimum of eight repetitions for each coordinate) was selected (FIG. 10).

After identifying the architecture with least error in the test data set, performance was further optimized by simulated annealing, countering the tendency of perceptrons to become trapped in local minima. Mimicking the random movement of atoms aligning in cooling metal, simulated annealing uses random perturbations of model parameters to find the global extremum in an objective function. Perturbations of steadily decreasing size (specified by a 'cooling profile') are guaranteed to find a global minimum with slow enough cooling, although, in practice, the necessary cooling profile is prohibitively slow. After training the perceptron until a minimum in RMS test set error, every weight, $\{w_{ih}\}$ and $\{w_{ho}\}$, was multiplied by a random coefficient. Training was then resumed to find a new minimum. If lower error was achieved, the new weights were accepted. This process was then repeated.

The value for each weight was determined by first sampling from a uniform distribution, $x \in [-1, 1]$, transformed by a hyperbolic function, $N=(1-x)/(1+x)$. Thus each weight was multiplied by $N \in [0, \infty]$, and was thus unchanged when x=0. The range sampled within x determined the amount of noise injected into the system, using values closer to zero over the course of cooling. The maximum value of x was determined by the temperature, T, and the minimum value was determined so that the mean squared value of N was unity:

$$\frac{1}{T-a} \int_a^T \left(\frac{x-1}{x+1}\right)^2 dx = 1 \qquad (12)$$

This choice of noise ensured that the sum of squares of the connection weights was unaltered by perturbation and that most weights were decreased, while a small selection was sporadically increased. A geometric cooling function (Eq. (13)) was used, which decreased over $K_1$ perturbation epochs; this entire annealing process was repeated $K_2$ times, each time with a slightly cooler temperature profile.

$$T_{k_1, k_2} = T_0 \cdot r^{(k_1 + 3k_2)} \qquad (13)$$

Figure 7:
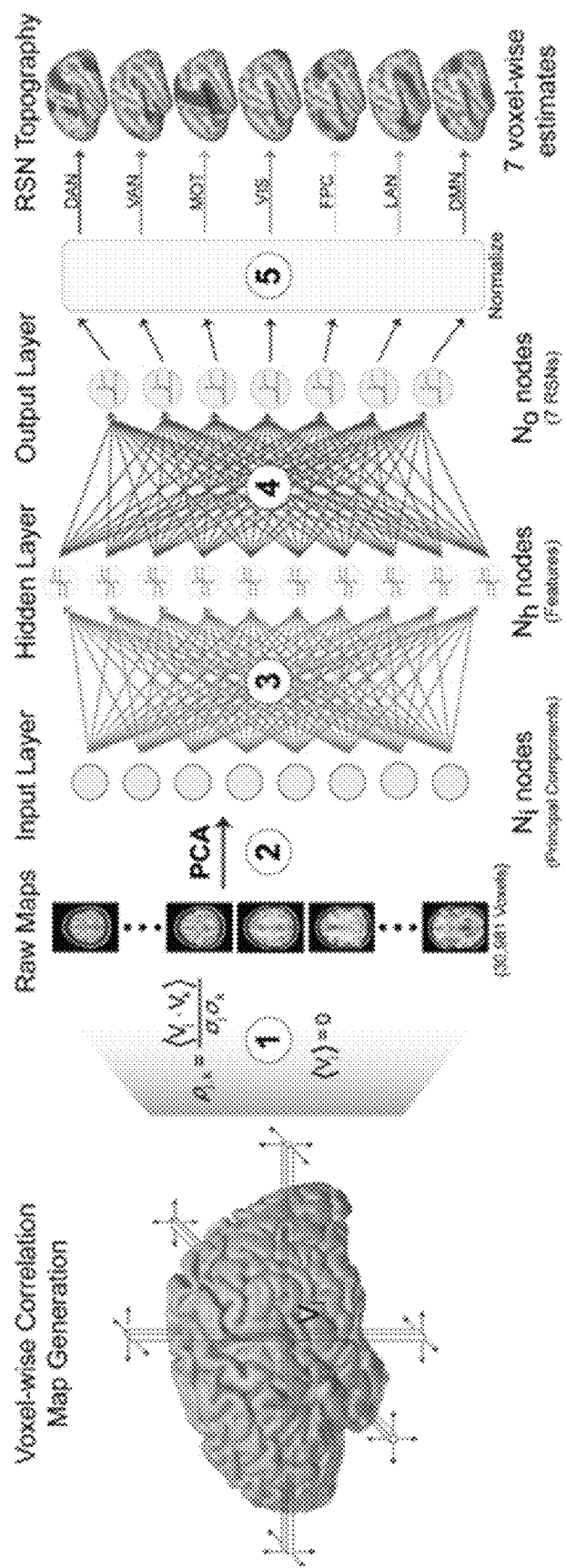
FIG. 7 is a schematic of a voxel-wise classification.

The following parameters were used: r=0.95, $T_0$=0.4, $K_1$=40, $K_2$=20. To map RSNs in individual subjects, a correlation map was generated for every voxel in the brain and then classified using the trained and optimized perceptron. An overall schematic of this process is depicted in FIG. 10. A correlation map was produced for every point in the brain by correlating every voxel's BOLD time-course with every other voxel in the brain. Each map was masked before classification to include only grey matter voxels producing a 65,549 (voxels within brain mask)×30,981 (voxels within grey matter mask) element matrix (FIG. 7). This data was then projected onto the eigenvectors of the training data, reducing the dimensionality to 65,549×2500 (FIG. 7). Thus, all correlation maps were represented in the same input data space for classifier training and testing. The reduced whole-brain connectivity data was then propagated through the perceptron, with the first layer reducing the data to 22 features (65,549×22; FIG. 7), and the second layer producing RSN estimates (65,549×8, FIG. 7). However, FIG. 7 depicts only 7 output classes because one of the 8 outputs is a nuisance component used only in post-processing.

Classifier output values are approximately uniformly [0, 1] distributed as a result of the logistic activation function on the output layer (Eq. (6)). Classifier values were then normalized within each voxel to sum to unity (FIG. 7). This normalization penalized voxels that had high classification values for multiple networks. The presence of a CSF classification component further penalized RSN estimates in voxels exhibiting CSF-related correlation patterns. Within each network, classifier values were then converted back to an exactly uniform [0, 1] distribution across voxels (rank-order transform). This transformation resulted in voxels ranked in membership for each network across the brain expressed as a percentile.

To visualize group level results on the cortical surface, RSN topography estimates were projected to the cortical mid-thickness surface for each subject (after surface-registration across subjects). Averages were then computed across surface nodes. The standard deviation of classifier values was also calculated node-wise to illustrate regions of high variability. These group-level results were projected onto the group-average inflated surface. To visualize group level results in sub-cortical structures, classifier values were averaged voxel-wise across subjects. Group-average images were then re-sampled to 1 mm cubic voxels and overlaid on a co-registered MNI152 atlas target.

In the exemplary embodiment, spatial correlation analysis (FIG. 8B) and principal component analysis (FIG. 8C) of the training data (the correlation maps produced for each seed ROI) revealed distinct clustering corresponding to RSNs. In the map-to-map spatial correlation matrix (averaged across subjects), training inputs showed high correlation with other inputs of the same RSN compared to inputs of other classes (FIG. 8B). Additionally, the map-to-map correlation matrix showed two major clusters, one corresponding to the DAN, VAN, VIS, and MOT networks, and the other corresponding to the FPC, LAN, and DMN networks. Projection of all 3,675 correlation maps into principal component space gave rise to partially overlapping clusters corresponding to 7 RSNs. In the PC1×PC2 plane (FIG. 6), DAN (purple) and DMN (red) showed little overlap and appeared at opposite ends of the PC1 axis. MOT (light blue) and VIS (green) clusters were highly overlapping in this plane, but showed little overlap in the PC3×PC4 plane.

FIGS. 9A-9F shows the training performance for the perceptron optimized for overall performance (2500 input PCs, 22 hidden layer nodes). For every correlation map, the perceptron output node values represent an estimate of membership for each RSN. The expectation value of all initial perceptron outputs is 0.5 (FIGS. 9A-9C) as the expected output value with zero-mean weights ($v_o$) is 0 (Eqs. (5) and (6)). As training progresses, within-class output values increase towards unity (e.g., DMN output node values for DMN inputs, red traces in FIG. 9A), while out-of-class output values decrease towards zero (DMN output value for non-DMN ROI-derived maps, all other traces in FIG. 9A).

Figure 9E:
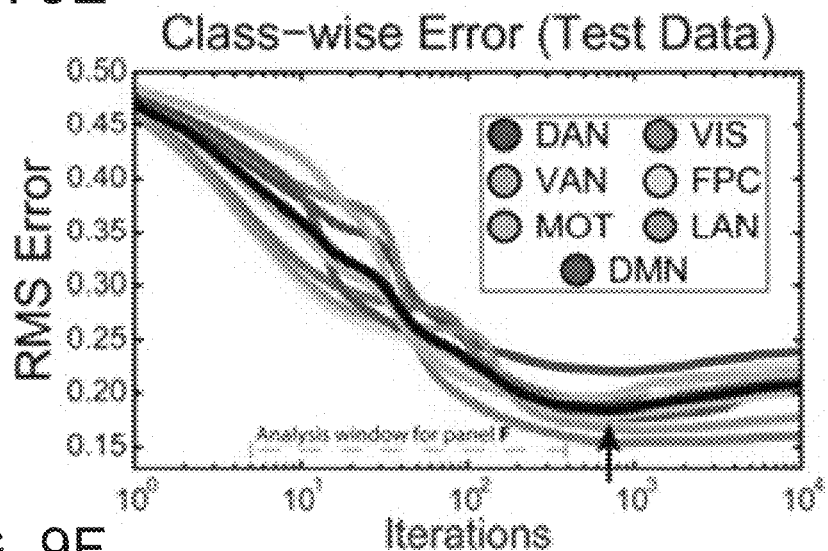
Figure 9F:
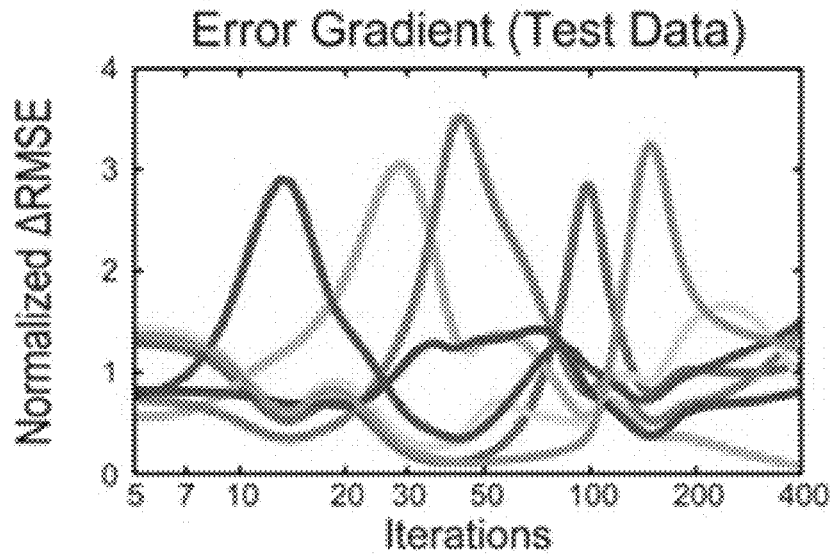

Area under the ROC curve (AUC) trajectories are shown in FIG. 9D. This quantity, averaged across RSN classes, began near chance (0.65 after one iteration) and rose in later iterations. For all networks, the AUC exhibited a transient decrement in performance early in training. This feature corresponded to transient changes of slope in RMS error but did not produce concavity (local minima) in RMS error (FIG. 9E). Class separation was achieved at varying numbers of iterations for different RSNs. Across all perceptron architectures, the default mode network (red trace) always achieved asymptotic performance earliest, and the language network (orange) latest. Asymptotic performance for CSF classification occurred much later than any true RSN. Performance on the test data initially followed training performance until reaching a global maximum (FIG. 9E). This maximum occurred at varying iteration indices for different RSNs. Training beyond this point resulted in over-fitting, manifesting as decreasing test data performance despite increasing training performance. Inputs that were previously correctly classified in the test data became incorrectly classified (FIGS. 9B and 9C).

Over a dense sampling of input and hidden layer sizes ($N_i \times N_h$), the perceptron was trained until the peak AUC could be determined (FIG. 10). The optimal overall performance for the perceptron was found at 2500 PCs and 22 hidden layer nodes (FIG. 10). The perceptron was trained with this architecture using 10 mm ROIs and the result was optimized through simulated annealing, yielding an over-all classification performance of 0.9822 (AUC) with 17.1% RMS error. The maximal AUC and minimal RMS error rates differed by network, as shown in Table 3.

TABLE 3

RSN classification performance.

| Network | Test (Optimization Set) | | Retest (Validation Set) | |
| --- | --- | --- | --- | --- |
| | Accuracy (AUC) | Error (RMS) | Accuracy (AUC) | Error (RMS) |
| DAN | 0.973 | 20.2% | 0.973 | 20.1% |
| VAN | 0.971 | 17.9% | 0.979 | 17.6% |
| SMN | 0.988 | 16.4% | 0.994 | 17.2% |
| VIS | 0.993 | 13.4% | 0.998 | 12.7% |
| FPC | 0.972 | 17.5% | 0.989 | 14.8% |
| LAN | 0.985 | 14.9% | 0.991 | 14.4% |
| DMN | 0.993 | 14.4% | 0.990 | 17.6% |
| Mean | 0.982 | 17.1% | 0.988 | 16.6% |

Figure 11A:
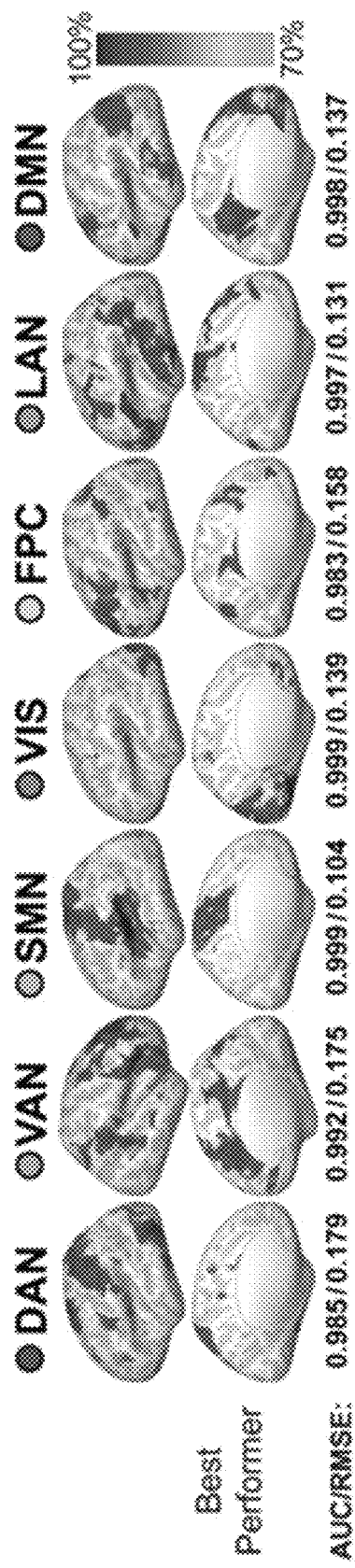
Figure 11B:
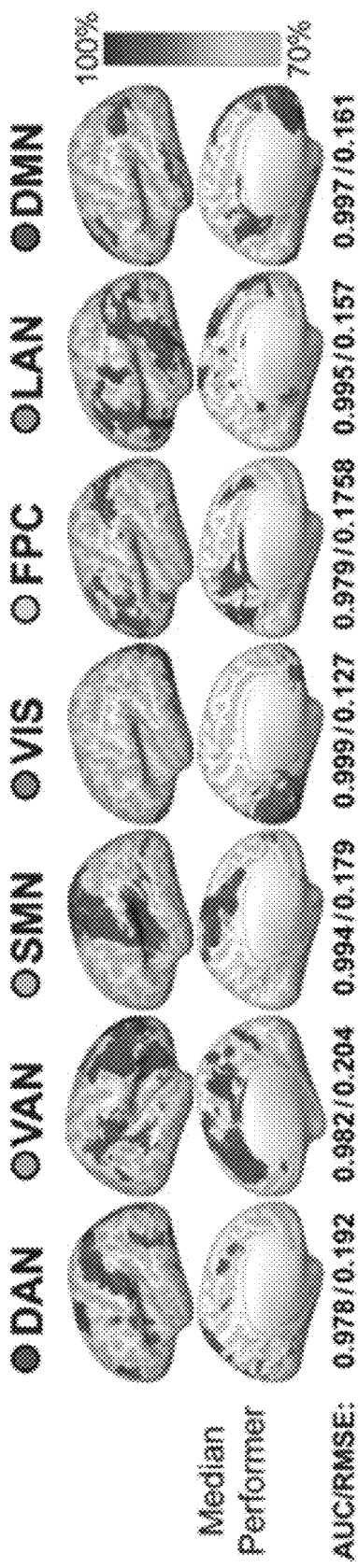

These values reflect MLP training with 10 mm radius seeds (FIGS. 14A and 14B) and optimization with simulated annealing. After completion of classifier training, voxel-wise connectivity patterns were classified in individual subjects in the test data set (FIG. 11A). RSN topography summaries were computed as winner-take-all maps (FIGS. 11A-11F and 12A-12C). Well-defined RSN topography was obtained in all subjects in the test and training groups. Specifically, the subject-wise mean and standard error of the AUC was 0.982±0.007, with the worst performing subject at 0.963. These figures corresponded to RMS error of 16.5±1.4% with the worst subject yielding 19.1%. RSNs were generally contiguous regions that conformed to previously described topography. The relationship of perceptron-defined RSNs to previous findings is discussed more fully below.

RSN topography estimates were averaged over all subjects in the training and test groups. FIGS. 12A-12C addresses both the central tendency (top row) of each group as well as inter-subject variability (middle row). Average network topographies had higher values near locations of ROIs used to generate training maps. This is expected because voxels within ROIs are likely to have similar correlation maps to the ROI. High classification values (in the top 25%) were also found in contiguous regions not used to generate training data. For example, a lateral temporal region was classified as a fronto-parietal control region, and a dorsal pre-motor region was classified into the language network. This type of result demonstrates external validity (or equivalently, generalizability) of perceptron classification, i.e., recovery of true features in RSNs not included in the training set. These features are also present in the results in individual subjects (FIG. 11A).

Figure 13:
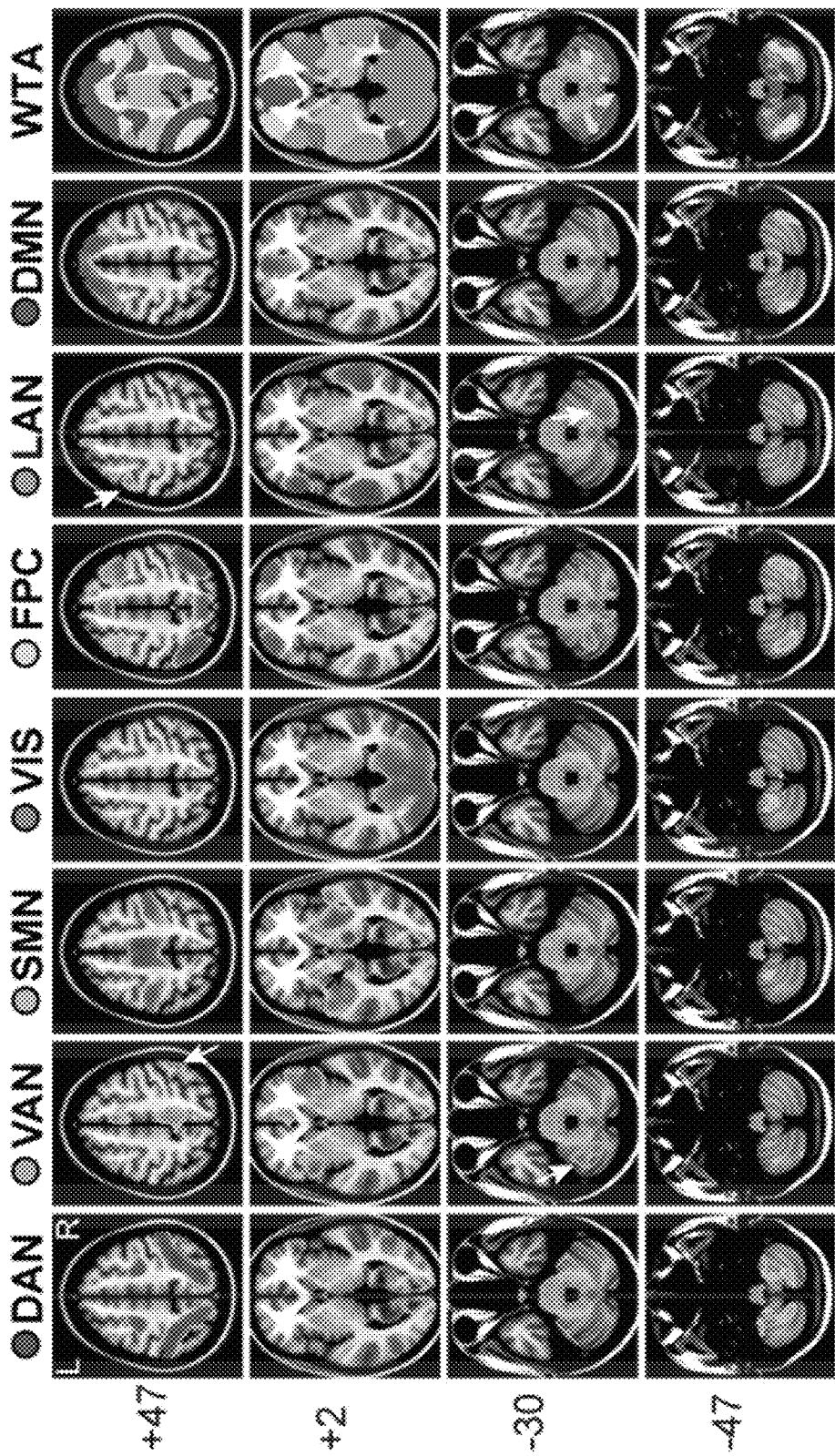
FIG. 13 is a scan of group averaged results.

Further evidence of external validity is shown in FIG. 13. For example, thalamic voxels approximately corresponding to nucleus ventralis posterior were classified as SMN, substantially in agreement. Similarly, voxels in the posterior cerebellum (Crus I and II) and the cerebellar tonsils were classified as DMN (FIG. 13, Z=−30, Z=−47), substantially in agreement. These results are notable because neither cerebellar nor thalamic ROIs were used to generate training data. Further, no cerebellar voxels were within the grey matter mask, which means that the classifier successfully identified cerebellar ROIs purely on the basis of cortical connectivity maps. The perceptron generated asymmetric classification in the cerebellum for the VAN and LAN networks (Z=−30), contralateral to their asymmetric cerebral representation (Z=+47).

The present results (individual and group RSN topographies) exhibit a high degree of face validity with respect to the training data and previously reported RSN results (FIGS. 11A-11F, 12A-12C, and 13). Thus, for example, components of the DMN used as seeds to generate the training data were classified as DMN in all subjects. This was true not only for easily classified networks (e.g., the DMN) but also for networks (e.g., VAN and LAN) that are inconsistently found by unsupervised procedures. The results shown in FIGS. 11A-11F illustrate that the perceptron reliably classified RSNs in each test set individual (AUC>0.971), even in cases in which the RMS error was relatively high (>0.2).

However, inter-individual differences were also evident (FIGS. 11A-11F). These differences systematically varied according to RSN and exhibited RSN-specific zones of high as well as low inter-individual variability (FIGS. 12A-12C). Easily classified voxels (i.e., with high classification values) generally showed the least inter-subject variability. Such regions, e.g., the posterior parietal component of the DMN (FIGS. 12A-12C), were surrounded by zones of high variability (e.g., ring around the angular gyms). The pre- and post-central gyri consistently showed high SMN classification values but were bordered by regions of high inter-subject SMN variability. Interestingly, inter-subject variability was low also in areas with classification values near 0, particularly in areas typically anticorrelated with other networks (e.g., low DAN variance in the angular gyms, a component of the DMN; low DMN variance in MT+, a component of the DAN).

At least four factors potentially contribute to observed inter-subject classifier output variability: (i) limited or compromised fMRI data, (ii) limitations intrinsic to the MLP (iii) true inter-individual differences in RSN topography and (iv) misregistration. Each of the possibilities is discussed below.

With regard to (i), the fMRI data used in the present work were obtained in healthy, cooperative young adults. Hence, the fraction of frames excluded because of head motion was low (about 4%). The total quantity of fMRI data acquired in each individual was, by current standards, generous. However, fMRI data quantity clearly affects MLP performance (see 4.4.2 below and FIGS. 14A-14B). Current results suggest that more data generally improves MLP performance. The impact of fMRI data quality and quantity on MLP performance in clinical applications remains to be determined. With regard to (ii), the observation of zones with high classifier values and low variance bordered by regions of high variance may reflect classification uncertainty in areas that truly represent more than one RSN, i.e., voxels with high participation coefficients.

With regard to (iii), on the other hand, the presently observed inter-individual differences may truly reflect individual variability in RSN topography. Previous work has demonstrated that inter-individual differences in task-evoked activity correspond to "transition zones" in resting state networks (e.g., the boundary between parietal DMN and DAN regions). These same regions appear in our inter-subject variance maps for both DMN and DAN (FIGS. 12A-12C). We also note that areas of high RSN classification variability (pre-frontal, parietal, lateral temporal) broadly correspond to regions exhibiting the greatest expansion over the course of human development and evolution. This correspondence may possibly be coincidental, but it is consistent with the hypothesis that later developing or evolutionarily more recent areas of the brain tend to be more variable across individuals.

Figure 16A:
FIGS. 16A and 16B are scans of topography estimates.
Figure 16B:

With regard to (iv), some proportion of the variability in observed RSN topography estimates may be explained by uncorrected anatomical variability. To investigate this possibility, the overall RSN standard deviation map (FIG. 16A) was compared to sulcal depth variability (FIG. 16B) and a weak spatial correlation (r=0.2) was found. By inspection, these maps were concordant only at a broad spatial scale: both showed low variability in primary motor/auditory/insular cortices and high variability elsewhere. Little correspondence was evident at finer scales (note lack of annular patterns in FIG. 16B). The degree to which anatomical variability contributes to spurious variance in RSN topography estimates may be addressed by measuring the degree to which non-linear or surface-based registration decreases inter-subject variance and increases overall classifier performance (higher AUC, lower RMSE).

Two distinct types of external validity, that is, correct classification outside the training set, are evident in our results. First, high overall classification performance was achieved for a priori seed-based correlation maps in test (98.2% AUC) and hold-out datasets (98.8% AUC). Performance was reliable in all subjects (97.1% worst-case AUC), which is critical in clinical applications. Second, and perhaps of greater scientific interest, the RSN estimates in areas not covered by seed regions were strongly concordant with previously reported task-based and resting-state fMRI results. For example, while no temporal FPC seed ROI was included in the training set, a posterior temporal gyms locus was classified as FPC the group level (FIGS. 12A-12C). Similarly, the MLP also identified the parahippocampal gyms as DMN and a dorsal pre-motor region that has been associated with articulation of speech as LAN. The right inferior cerebellum was first associated with language function by PET studies of semantic association tasks. Identification of this region here as part of the LAN network (FIG. 13, WTA, Z<−30) is doubly significant. First, no cerebellar seeds were used to generate training data and, further, cerebellar voxels were excluded from the gray matter mask, hence, were not seen by the classifier. Second, lateralized RSN components typically are not found by unsupervised seed-based correlation mapping.

These findings highlight the capabilities of supervised classifiers applied to the problem of identifying RSNs in individuals. The representation of language (primarily Broca's and Wernicke's areas) has been extensively studied using task-based fMRI and correlation mapping with a priori selected ROIs. However, the language network, as presently defined, typically is not recovered as such by unsupervised methods. Rather, components of the LAN are generally found only at fine-scale RSN descriptions. Thus, an RSN including Broca's and Wernicke's areas appears as the 11th of 23 components in; these same areas were identified as VAN and DMN. A component consistent with the presently defined LAN at a hierarchical level of 11 (but not 7) clusters has been found. Thus, the exemplary experiment, work demonstrates the potential of supervised classifiers to find networks that are subtle features of the BOLD correlation structure, possibly even minor sub-components within hierarchically organized RSNs, that nevertheless have high scientific and/or clinical value. The LAN was specifically included here to meet the clinical imperative of localizing language function in the context of pre-operative neurosurgical planning.

In the exemplary embodiment, the hierarchical scale of an RSN is reflected in training performance trajectories (FIGS. 9E and F): in all ($N_i \times N_h$) architecture variants, the DMN was the first to be separated from other RSNs. The DMN arguably is the most robust feature in the correlation structure of intrinsic brain activity. Its topography is very similar across RSN mapping strategies (specifically, spatial ICA and seed-based correlation mapping. Here, the DMN and regions anticorrelated with the DMN were well separated along the first principal component of the training data (FIG. 6).

After the DMN, the sensorimotor and visual networks were next to achieve separation during classifier training. These networks are often seen at the next level down in the RSN hierarchy as offshoots of the anti-DMN or extrinsic system. The dorsal attention network achieved only a small peak in error descent compared to other 'extrinsic' networks, though this occurred in close proximity (note overlap of DAN, MOT, VIS peaks in FIG. 9F). In contrast, the LAN and VAN were last to achieve separation during training. This corresponds to the observation that LAN and VAN systems are typically found by analyses extending to lower levels of the RSN hierarchy.

In the exemplary embodiment, the observer is a multi-layer perceptron and the task is to assign RSN labels to each voxel. Performance is evaluated in terms of mean squared classification error and ROC analyses. It follows that MLP performance can be used to evaluate image quality across a wide range of variables, e.g., scanners, and acquisition parameters (e.g., TR, run length, resolution), preprocessing strategies (nuisance regression, filtering, spatial smoothing) and data representations (surface or volume based). This principle is demonstrated by systematically evaluating MLP performance in relation to quantity of fMRI data and seed ROI size.

Figure 14A:
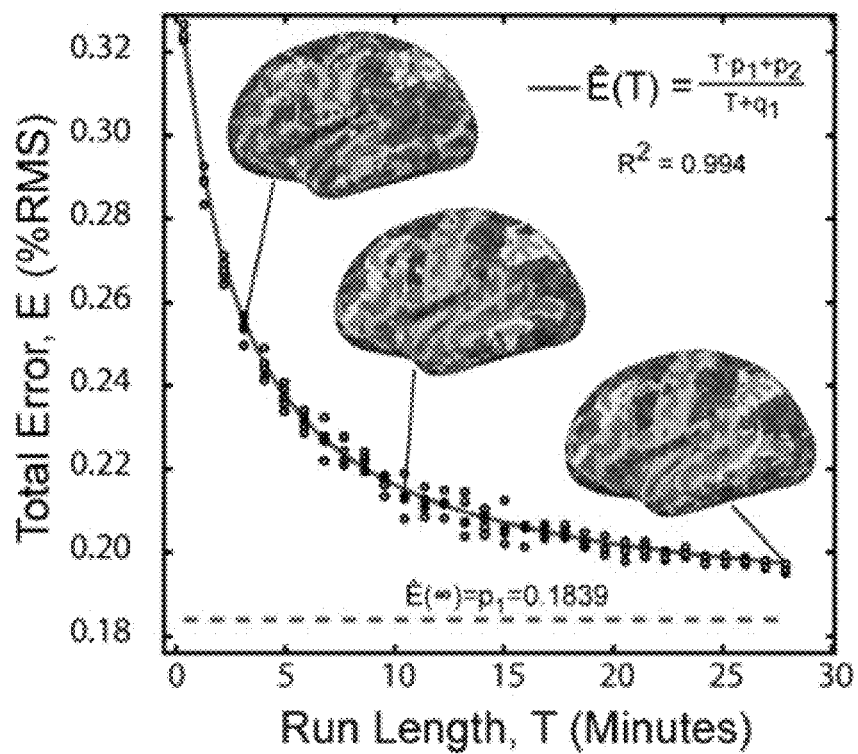
FIGS. 14A and 14B are graphs of exemplary evaluations.

The relation between total quantity of fMRI data and MLP performance (test dataset RMS error) is shown in FIG. 14A. The plotted points represent five replicate MLP training/test runs. RMS error as a function of data quantity was well fit ($R^2=0.994$) by a three-parameter empirically derived hyperbolic function. The parameterized function implies that classifier error monotonically decreases with increasing total fMRI data length but ultimately asymptotes at ~18% RMS (with 5 mm radius seeds and no simulated annealing). The existence of this asymptote may indicate that resting-state brain networks are inherently non-separable in the sense of classification. This is consistent with the notion of "near decomposability" of hierarchical systems formed by multiple, sparsely inter-connected modules. This concept has since been extended to brain networks.

Figure 14B:
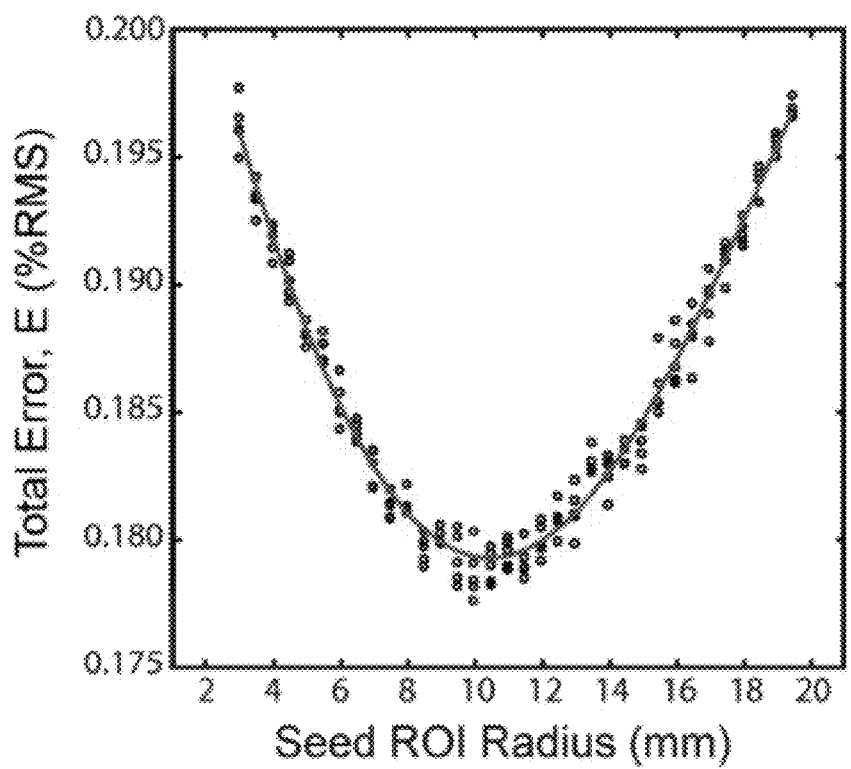

The relationship between seed ROI radius and RMS classification error was explored using a perceptron architecture optimized with 5 mm radius seeds (2500 PCs, 22 hidden nodes). All seeds were masked to include only gray matter voxels. The results of systematically varying seed ROI size are shown in FIG. 14B. A clear minimum in RMS error was obtained with seeds of approximately 10 mm radius. Voxel-wise RSN topographies were qualitatively similar across ROI sizes, but larger seeds generated less noisy RSNs with more pronounced peaks. This result is unexpected, as it deviates from the current standard practice of using approximately 6 mm radius seeds. There are several possible explanations for the present results. Large seeds may best match the characteristic dimensions of RSNs in the 7-network level description of the brain. Alternatively, large seeds may compensate for misregistration in affine-coregistered, volume-preprocessed data. Smaller seeds may be used in classifiers operating on non-linear, surface-coregistered, geodesically smoothed data. The results shown in FIG. 14B reflect the effect of seed radius on the correlation maps used to train the MLP. It is formally possible for a corrupted training set to yield a better classifier as evaluated by test set classification error. Thus, the results shown in 14B should not be interpreted as unambiguously indicating that 10 mm radius seeds are optimal for correlation mapping.

Inter-individual differences in computed RSN topographies may reflect multiple factors. Cross-gyral contamination due to the relatively large voxels used in this study (4 mm acquisition, 3 mm post-processing analyses) may limit the precision of RSN classification in the dataset. Potential strategies for validating perceptron-derived results include comparison with measures of structural (axonal) connectivity and invasive electrophysiologic recording.

The MLP RSN classifier operates at the voxel level via computed correlation maps. After training, it reliably identifies RSN topographies in individual subjects. Classification is rapid (2 minutes using Matlab running on Intel i7 processors) and automated, hence suitable for deployment in clinical environments. After training, classification is independent of any particular seed. Therefore, the trained MLP is expected to be robust to anatomical shifts and distortions, for example, owing to enlarged ventricles and mass effects or even loss of neural tissue (e.g., stroke).

In this experiment, the classifier was trained to operate in 3D image space for compatibility with clinical imaging formats. However, the MLP concept can be readily adapted to operate on correlation maps represented on the cortical surface. Similarly, voxel-wise classifiers can be trained to classify subjects despite anatomical abnormalities (e.g., brain tumors) by altering the domain of the training set, i.e., excluding tumor voxels. Another potentially useful MLP modification would be removal by regression of the relationship between correlation and distance to the seed. Such regression may decrease the reliance of the classifier on local connectivity, thereby reducing susceptibility to corruption by movement artifact.

As compared to known systems that are used for brain mapping, the embodiments described herein enable a substantially efficient task-less system for brain mapping. More specifically, the embodiments described herein include a computing device for use in a system for mapping brain activity of a subject that generally comprises a processor. The processor is programmed to select a plurality of measurements of brain activity that is representative of at least one parameter of a brain of the subject during a resting state. Moreover, the processor is programmed to compare at least one data point from each of the measurements with a corresponding data point from a previously acquired data set from at least one other subject. The processor is also programmed to produce at least one map for each of the measurements based on the comparison of the resting state data point and the corresponding previously acquired data point. The processor may also be programmed to categorize the brain activity in a plurality of networks in the brain based on the map. By using previously acquired data points to categorize the brain activity in a plurality if networks in the brain of the subject, task-based techniques may be avoided. Moreover, by having the processor select the plurality of measurements, a user may no longer need to spend a considerable amount of time determining which measurements, such as voxels, to select.

Exemplary embodiments of the system, apparatus, and method are described above in detail. The system, apparatus, and method are not limited to the specific embodiments described herein, but rather, components of the system and apparatus, and/or steps of the methods may be utilized independently and separately from other components and/or steps described herein. For example, but not limited to, the system may also be used in combination with other apparatus, systems, and methods, and is not limited to practice with only the system as described herein. Rather, the exemplary embodiment can be implemented and utilized in connection with many other applications.

Although specific features of various embodiments of the invention may be shown in some drawings and not in others, this is for convenience only. In accordance with the principles of the invention, any feature of a drawing may be referenced and/or claimed in combination with any feature of any other drawing.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

In operation, a computer executes computer-executable instructions embodied in one or more computer-executable components stored on one or more computer-readable media to implement aspects of the invention described and/or illustrated herein.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method for mapping a set of predefined brain resting state networks (RSNs) in a brain of an individual subject, the method comprising:

receiving measurements of brain activity for an individual subject during a resting state, the measurements having been made by a functional magnetic resonance imaging (fMRI) device using a blood oxygen level dependent (BOLD) contrast;

generating a voxel-wise correlation map based on the received resting state fMRI brain activity measurements for the individual subject, the voxel-wise correlation map comprising an [n x m] matrix of correlations between each resting state BOLD time-course for voxels 1 through n and each resting state BOLD time-course for voxels 1 through m;

propagating data from the voxel-wise correlation map through a trained artificial neural network to generate, at output nodes of the trained artificial neural network, an output of voxel-wise estimates of a topography of each of the predefined brain RSNs in the individual subject, wherein the voxel-wise estimates comprise values representing an estimate of a voxel's membership for each voxel within each of the predefined brain RSNs, and wherein the artificial neural network is trained with correlation map patterns representing the predefined brain RSNs from previously acquired measurements of brain activity for subjects during a resting state made with an fMRI device using a BOLD contrast; and transforming, the output of voxel-wise estimates of the topography of each of the predefined brain RSNs in the individual subject into a data format to facilitate visualization of maps of the RSN topography.

2. The computer-implemented method of claim 1, wherein the trained artificial neural network comprises a multilayer perceptron comprising input, hidden, and output layers, each layer consisting of nodes fully connecting to the next layer in an all-to-all feed-forward configuration.

3. The computer-implemented method of claim 1, wherein the artificial neural network was trained using a supervised training process.

4. The computer-implemented method of claim 3, wherein the supervised training process uses a plurality of training samples each comprising a correlation map for a particular brain region-of-interest (ROI) and an a priori RSN label assigned to the training sample that corresponds to RSN membership of the particular brain ROI.

5. The computer-implemented method of claim 4, wherein the supervised training process comprises propagating training samples through the artificial neural network and evaluating error in output values estimating RSN membership.

6. The computer-implemented method of claim 1, further comprising performing initial preprocessing including slice-dependent time shifts, elimination of systematic odd-even slice intensity differences due to interleaved acquisition, and correction for head movement.

7. The computer-implemented method of claim 1, wherein the predefined brain RSNs are predefined by canonical spatial patterns in correlation maps based on resting-state fMRI brain activity measurements.

8. The computer-implemented method of claim 1, wherein the predefined brain RSNs comprise a sensorimotor network.

9. The computer-implemented method of claim 1, wherein the predefined brain RSNs comprise a language network.

10. The computer-implemented method of claim 1, wherein the predefined brain RSNs comprise a vision network.

11. The computer-implemented method of claim 1, wherein the predefined brain RSNs comprise a sensorimotor network, a language network, and a vision network.

12. The computer-implemented method of claim 11, wherein the predefined brain RSNs further comprise at least one attention network.

13. The computer-implemented method of claim 1, wherein the predefined brain RSNs further comprise at least one attention network.

14. The computer-implemented method of claim 1, wherein the predefined brain RSNs comprise a default mode network.

15. The computer-implemented method of claim 1, wherein the predefined brain RSNs comprise a frontoparietal control network.

16. The computer-implemented method of claim 1, wherein transforming the output of voxel-wise estimates results in voxels ranked in membership for each RSN across the brain expressed as a percentile.

17. A system for task-less mapping of a set of predefined brain resting state networks (RSNs) in a brain of an individual subject comprising:
a computing device including:
a memory device storing instructions; and
a processor coupled to the memory device, the instructions stored in the memory device configuring the processor to:
receive measurements of brain activity for an individual subject during a resting state, the measurements having been made by a functional magnetic resonance imaging (EMRI) device using a blood oxygen level dependent (BOLD) contrast;
generate a voxel-wise correlation map based on the received resting state fMRI brain activity measurements for the individual subject, the voxel-wise correlation map comprising an [n x m] matrix of correlations between each resting state BOLD time-course for voxels 1 through n and each resting state BOLD time-course for voxels 1 through m;
propagate data from the voxel-wise correlation map through a trained artificial neural network to generate, at output nodes of the trained artificial neural network, an output of voxel-wise estimates of a topography of each of the predefined brain RSNs in the individual subject, wherein the voxel-wise estimates comprise values representing an estimate of a voxel's membership for each voxel within each of the predefined brain RSNs, and wherein the artificial neural network is trained with correlation map patterns representing the predefined brain RSNs from previously acquired measurements of brain activity for subjects during a resting state made with an fMRI device using a BOLD contrast; and
transform, the output of voxel-wise estimates of the topography of each of the predefined brain RSNs in the individual subject into a data format to facilitate visualization of maps of the RSN topography.

18. The system of claim 17, wherein the trained artificial neural network comprises a multilayer perceptron comprising input, hidden, and output layers, each layer consisting of nodes fully connecting to the next layer in an all-to-all feed-forward configuration.

19. The system of claim 17, wherein the artificial neural network was trained using a supervised training process.

20. The system of claim 19, wherein the artificial neural network was trained using the supervised training process by:
using a plurality of training samples each comprising a correlation map for a particular brain region-of-interest (ROI) and an a priori RSN label assigned to the training sample that corresponds to RSN membership of the particular brain ROI; and
propagating training samples through the artificial neural network and evaluating error in output values estimating RSN membership.

21. The system of claim 17, wherein the predefined brain RSNs are predefined by canonical spatial patterns in correlation maps based on resting-state fMRI brain activity measurements.

22. The system of claim 17, wherein the predefined brain RSNs comprise a sensorimotor network, a language network, and a vision network.

23. The system of claim 17, wherein the predefined brain RSNs further comprise at least one attention network.

24. The system of claim 17, wherein the predefined brain RSNs comprise a default mode network.

* * * * *